US011433238B2

(12) United States Patent
Fisher et al.

(10) Patent No.: US 11,433,238 B2
(45) Date of Patent: Sep. 6, 2022

(54) TREATMENT OF PHANTOM LIMB PAIN AND DIABETIC NEUROPATHY PAIN, AND INCREASING PROSTHETIC CONTROL, BY STIMULATION OF DORSAL ROOTLETS AND LATERAL SPINAL CORD

(71) Applicant: University of Pittsburgh—Of the Commonwealth System of Higher Education, Pittsburgh, PA (US)

(72) Inventors: Lee Erik Bartholomew Fisher, Pittsburgh, PA (US); Robert A. Gaunt, Pittsburgh, PA (US); Douglas J. Weber, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 320 days.

(21) Appl. No.: 16/845,691

(22) Filed: Apr. 10, 2020

(65) Prior Publication Data
US 2020/0324113 A1   Oct. 15, 2020

Related U.S. Application Data

(60) Provisional application No. 62/832,210, filed on Apr. 10, 2019.

(51) Int. Cl.
| | |
|---|---|
| *A61N 1/36* | (2006.01) |
| *A61F 2/72* | (2006.01) |
| *A61F 2/58* | (2006.01) |
| *A61F 2/66* | (2006.01) |
| *A61B 5/00* | (2006.01) |

(52) U.S. Cl.
CPC .......... *A61N 1/36071* (2013.01); *A61B 5/486* (2013.01); *A61B 5/6811* (2013.01); *A61F 2/586* (2013.01); *A61F 2/66* (2013.01); *A61F 2/72* (2013.01); *A61N 1/36021* (2013.01); *A61N 1/36031* (2017.08); *A61N 1/36139* (2013.01); *A61B 5/4851* (2013.01); *A61F 2002/665* (2013.01)

(58) Field of Classification Search
None
See application file for complete search history.

(56) References Cited

U.S. PATENT DOCUMENTS

| 7,302,296 B1 * | 11/2007 | Hoffer ................ A61N 1/36021 |
| | | 607/46 |
| 7,502,651 B2 | 3/2009 | Kim et al. |
| 7,580,753 B2 | 8/2009 | Kim et al. |

(Continued)

OTHER PUBLICATIONS

Chandrasekaran et al., "Sensory Restoration by Epidural Stimulation of Dorsal Spinal Cord in Upper-Limb Amputees," *Medrxiv*: Oct. 1-15, 2019.

(Continued)

*Primary Examiner* — Kennedy Schaetzle
(74) *Attorney, Agent, or Firm* — Klarquist Sparkman, LLP

(57) ABSTRACT

The present disclosure provides a method of reducing phantom limb pain or diabetic neuropathy pain, and increasing prosthetic control, by stimulating dorsal spinal rootlets and/or lateral spinal cord adjacent to the dorsal rootlets, of sensory neurons innervating the limb with the phantom limb pain or diabetic neuropathy pain, or the prosthetic.

28 Claims, 15 Drawing Sheets
(14 of 15 Drawing Sheet(s) Filed in Color)

(56) References Cited

U.S. PATENT DOCUMENTS

| | | | |
|---|---|---|---|
| 8,229,565 B2 | 7/2012 | Kim et al. | |
| 8,849,422 B2 | 9/2014 | Pianca | |
| 9,205,260 B2 | 12/2015 | Kim et al. | |
| 9,622,671 B2 | 4/2017 | Weber et al. | |
| 2010/0152808 A1* | 6/2010 | Boggs, II | A61N 1/0456 607/46 |
| 2011/0065505 A1* | 3/2011 | Solanki | A61B 5/4064 463/31 |
| 2012/0302821 A1* | 11/2012 | Burnett | A61N 1/36021 600/13 |
| 2013/0317587 A1 | 11/2013 | Barker | |
| 2016/0143751 A1* | 5/2016 | Chestek | A61F 2/72 623/25 |

OTHER PUBLICATIONS

Charkhkar et al., "High-Density Peripheral Nerve Cuffs Restore Natural Sensation to Individuals with Lower-Limb Amputations," *J Neural Eng.* 15.5: 056002, Oct. 2018 (14 pages).

Clippinger et al., "Afferent Sensory Feedback for Lower Extremity Prothesis," *Clin Orthop Relat Res.* 169: 202-206, Sep. 1982.

Cruccu et al., "EFNS Guidelines on Neurostimulation Therapy for Neuropathic Pain," *Eur J Neurol.* 14.9: 952-970, Sep. 2007.

Davis et al., "Restoring Motor Control and Sensory Feedback in People with Upper Extremity Amputations Using Arrays of 96 Microelectrodes Implanted in the Median and Ulnar Nerves," *J Neural Eng.* 13.3: 036001, Jun. 2016 (15 pages).

Deer et al., "A Prospective Study of Dorsal Root Ganglion Stimulation for the Relief of Chronic Pain," *Neuromodulation* 16.1: 67-72, Jan.-Feb. 2013.

Dhillon et al., "Residual Function in Peripheral Nerve Stumps of Amputees: Implications for Neural Control of Artificial Limbs," *J Hand Surg Am.* 29.4: 605-615, Jul. 2004.

Dhillon et al., "Effects of Short-Term Training on Sensory and Motor Function in Severed Nerves of Long-Term Human Amputees," *J Neurophysiol.* 93.5: 2625-2633, May 2005.

Dhillon and Horch, "Direct Neural Sensory Feedback and Control of a Prosthetic Arm," *IEEE Trans Neural Syst Rehabil Eng.* 13.4: 468-472, Dec. 2005.

Eldabe et al., "Dorsal Root Ganglion (DRG) Stimulation in the Treatment of Phantom Limb Pain (PLP)," *Neuromodulation* 18.7: 610-617, Oct. 2015.

Horch et al., "Object Discrimination with an Artificial Hand Using Electrical Stimulation of Peripheral Tactile and Proprioceptive Pathways with Intrafascicular Electrodes," *IEEE Trans Neural Syst Rehabil Eng.* 19.5: 483-489, Oct. 2011.

Kuiken et al., "Targeted Reinnervation for Enhanced Prosthetic Arm Function in a Woman with a Proximal Amputation: A Case Study," *Lancet* 369.9559: 371-380, Feb. 2007.

Kuiken et al., "Redirection of Cutaneous Sensation from the Hand to the Chest Skin of Human Amputees with Targeted Reinnervation," *Proc Natl Acad Sci U.S.A* 104.50: 20061-20066, Dec. 2007.

Kumar and Rizvi, "Historical and Present State of Neuromodulation in Chronic Pain," *Curr Pain Headache Rep.* 18.1: 387, Jan. 2014 (7 pages).

Liem et al., "A Multicenter, Prospective Trial to Assess the Safety and Performance of the Spinal Modulation Dorsal Root Ganglion Neurostimulator System in the Treatment of Chronic Pain," *Neuromodulation* 16.5: 471-482, Sep.-Oct. 2013.

Marasco et al., "Robotic Touch Shifts Perception of Embodiment to a Prosthesis in Targeted Reinnervation Amputees," *Brain* 134.Pt 3: 747-758, Mar. 2011.

Marasco et al., "Sensory Capacity of Reinnervated Skin After Redirection of Amputated Upper Limb Nerves to the Chest," *Brain* 132.Pt 6: 1441-1448, Jun. 2009.

Okorokova et al., "Biomimetic Encoding Model for Restoring Touch in Bionic Hands through a Nerve Interface," *J Neural Eng.* 15.6: 066033, Dec. 2018 (19 pages).

Petersen et al., "Phantom Limb Pain: Peripheral Neuromodulatory and Neuroprosthetic Approaches to Treatment," *Muscle & Nerve* 59.2: 154-167, Aug. 2018.

Raspopovic et al., "Restoring Natural Sensory Feedback in Real-Time Bidirectional Hand Prostheses," *Sci Transl Med.* 6: 222ra19, Feb. 2014 (10 pages).

Rossini et al., "Double Nerve Intraneural Interface Implant on a Human Amputee for Robotic Hand Control," *Clin Neurophysiol.* 121.5: 777-783, May 2010.

Strbac et al., "Short- and Long-Term Learning of Feedforward Control of a Myoelectric Prosthesis with Sensory Feedback by Amputees," *IEEE Trans Neural Syst Rehabil Eng.* 25.11: 2133-2145, Nov. 2017.

Tan et al., "A Neural Interface Provides Long-Term Stable Natural Touch Perception," *Sci Transl Med.* 6: 257ra138, Oct. 2014 (25 pages).

Tan et al., "Stability and Selectivity of a Chronic, Multi-Contact Cuff Electrode for Sensory Stimulation in Human Amputees," *J Neural Eng.* 12.2: 026002, Apr. 2015 (19 pages).

Valle et al., "Biomimetic Intraneural Sensory Feedback Enhances Sensation Naturalness, Tactile Sensitivity, and Manual Dexterity in a Bidirectional Prosthesis," *Neuron* 100: 37-45, Oct. 2018.

Zhang et al., "Somatotopical Feedback Versus Non-Somatotopical Feedback for Phantom Digit Sensation on Amputees Using Electrotactile Stimulation," *J Neuroeng Rehabil.* 12: 44, May 2015 (11 pages).

\* cited by examiner

Subject 1    Subject 2    Subject 3    Subject 4

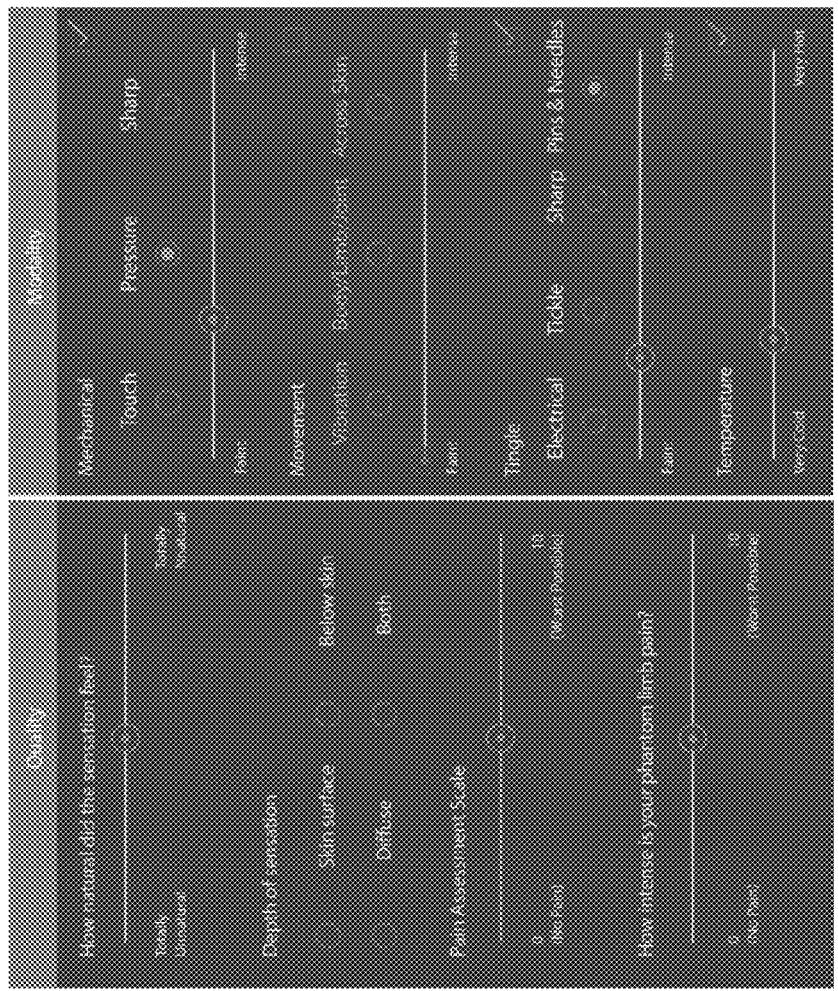
FIG. 8C
FIG. 8B
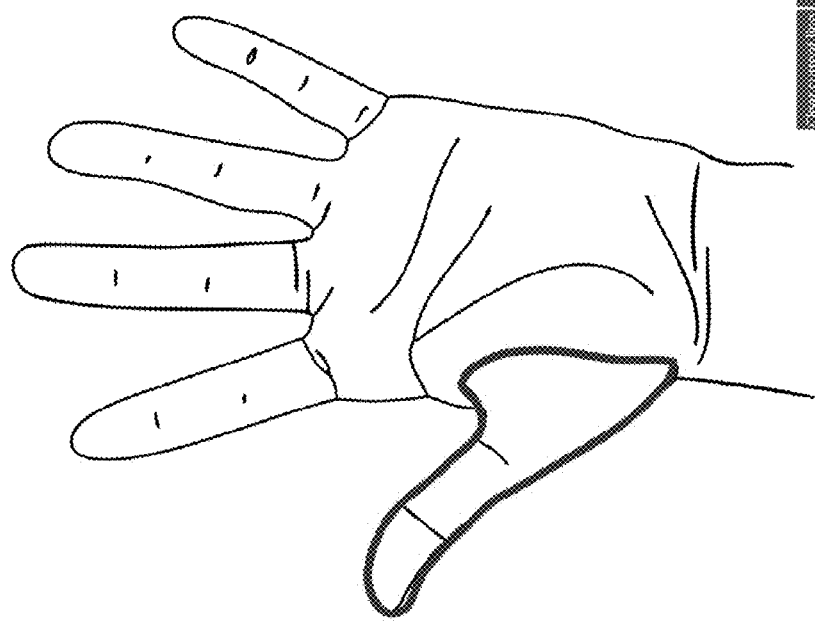
FIG. 8A

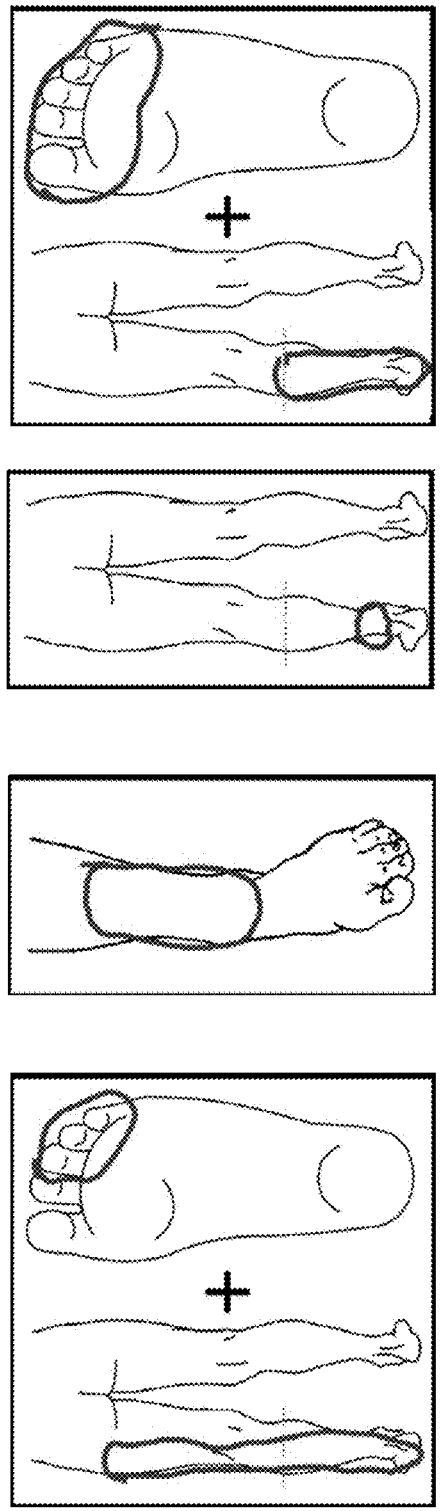
FIG. 13 Location of evoked sensations in missing limb (two weeks post-implantation)

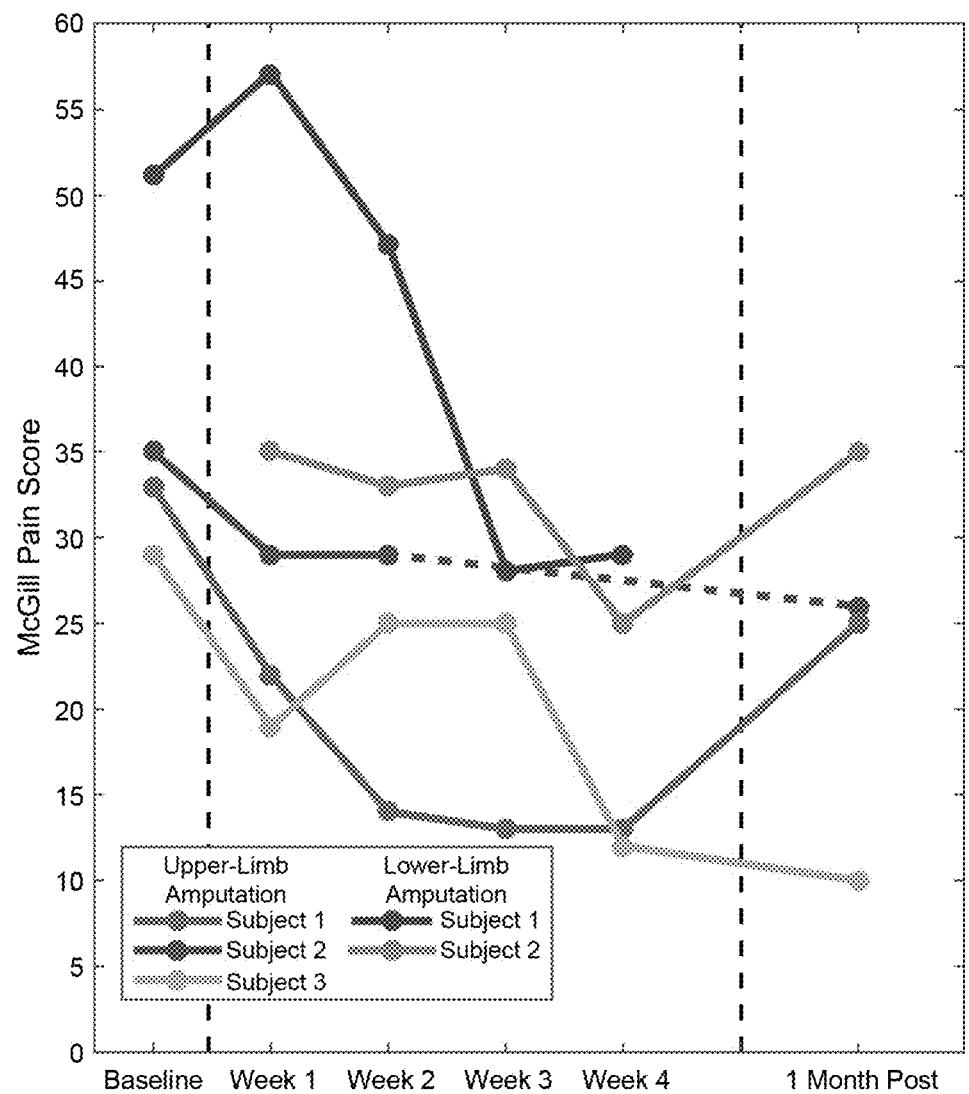

TREATMENT OF PHANTOM LIMB PAIN AND DIABETIC NEUROPATHY PAIN, AND INCREASING PROSTHETIC CONTROL, BY STIMULATION OF DORSAL ROOTLETS AND LATERAL SPINAL CORD

CROSS REFERENCE TO RELATED APPLICATION

This application claims priority to U.S. Provisional Application No. 62/832,210, filed Apr. 10, 2019, which is incorporated by reference in its entirety.

ACKNOWLEDGMENT OF GOVERNMENT SUPPORT

This invention was made with government support under Grant Nos. NS100541 and NS072342 awarded by the National Institutes of Health, Grant No. W911-NF-15-2-0016 awarded by the Army Research Office, and Grant No. N66001-11-C-4171 awarded by the Navy Research Office. The government has certain rights in the invention.

FIELD

The present disclosure relates to a method of treating phantom limb pain and diabetic neuropathic pain in a subject by stimulating the dorsal rootlets and lateral spinal cord, as well as a method of increasing control of a prosthetic limb in a subject.

BACKGROUND

There are over 1.5 million patients with limb amputation in the United States and the number is projected to increase to 2.2 million by 2020. Although there have been major advances in prosthetics and control of pain following amputation, there exist notable problems such as phantom limb pain and continued difficulties with prosthetic control.

Additionally, diabetic neuropathy is a complication of diabetes observed in an ever increasing number of patients in the United States. Although treatments for diabetic neuropathy symptoms are available, the condition is complicated and progressive and existing treatments often fail to adequately control symptoms. Thus, a need exists for new and improved treatments for diabetic neuropathy.

SUMMARY

Methods for treating phantom limb pain or diabetic neuropathy pain in a subject are disclosed. The method comprises providing a therapeutically effective amount of stimulation to dorsal rootlets, or lateral spinal cord adjacent to the dorsal rootlets, of one or more sensory neurons innervating a limb of the subject with the phantom limb pain or the diabetic neuropathy pain. The stimulation is provided with one or more electrodes of a neurostimulator that are implanted at the dorsal rootlets or the lateral spinal cord adjacent to the dorsal rootlets of the one or more sensory neurons innervating the limb of the subject with the phantom limb pain or the diabetic neuropathy pain. The one or more electrodes are activated to provide the stimulation in response to activation of a sensor detecting movement and/or position of the limb, or movement and/or position of a physical or virtual prosthesis of the limb, with the phantom limb pain or diabetic neuropathy pain. Administering the therapeutically effective amount of the stimulation to the subject reduces the phantom limb pain or diabetic neuropathy pain in the subject.

In several embodiments, the method further comprises calibrating the stimulation administered to the subject to induce sensations of pressure, touch, or joint movement at the location of the phantom limb pain or diabetic neuropathy pain in the subject. In further embodiments, the stimulation administered to the subject does not induce paresthesia in the limb with the phantom limb pain or diabetic neuropathy pain.

A method for increasing control of a prosthetic limb of a subject is also provided herein. The method comprises providing a therapeutically effective amount of stimulation to dorsal rootlets, or lateral spinal cord adjacent to the dorsal rootlets, of sensory neurons innervating an amputated limb of the subject, wherein the subject uses a prosthesis of the amputated limb. The stimulation is provided with one or more electrodes of a neurostimulator that are implanted at the dorsal rootlets or the lateral spinal cord adjacent to the dorsal rootlets of the sensory neurons innervating the amputated limb. The one or more electrodes are activated to provide the stimulation in response to activation of a sensor detecting movement and/or position of a stump of the limb or the prosthesis or in response to movement and/or position of virtual prosthesis of the limb. Administering the therapeutically effective amount of the stimulation to the subject improves control of the prosthesis of the limb by the subject. In several embodiments, the method further comprises calibrating the stimulation administered to the subject to induce sensations of pressure, touch, or joint movement in the amputated limb of the subject. In further embodiments, the stimulation administered to the subject does not induce paresthesia in the amputated limb.

The foregoing and other features of this disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 4A) Schematic of traditional dermatomes. Dotted lines indicate approximate location of anatomical segments. (FIG. 4B) Heat maps show the relative proportion of electrodes located at different spinal levels to the total number of percepts emanating from a specific region of the arm. The spinal level of each electrode was defined by the position of the cathode with respect to the spinal levels as seen in the X-rays. Spinal levels that have no electrodes nearby are marked with gray hatching.

(FIG. 5A) Example data from a detection task for a single electrode from Subject 2. Data were collected using a threshold tracking method and a psychometric function was fit to the data. The detection threshold was determined to be 982 µA. (FIG. 5B) Histogram showing the distribution of all detection thresholds for Subjects 1 (blue), 2 (red), 3 (yellow) and 4 (purple). (FIG. 5C) Example data from Subject 3 of a free magnitude estimation task carried out on two different days (open and filled circles respectively) for a single electrode. Perceived intensity varied linearly with stimulus amplitude for each individual testing session (dashed and solid yellow lines) as well as when taken together (black solid line). (FIG. 5D) Summary of magnitude estimation results where the coefficient of determination ($R^2$) and slope of the linear fit are displayed for all relevant electrodes. There was a weak correlation ($R=0.028$) better $R^2$ and slope. (FIG. 5E) Example data for the just-noticeable differences at two different standard amplitudes for 1 electrode in subject 3 (yellow) and 5 electrodes in subject 4 (purple). Error bars represent SD.

(FIG. 6A) Composite image showing the changes in the position of the SCS leads in the epidural space. The intraoperative fluoroscopy image (contacts appear black) showing the position of the leads immediately after implantation is superimposed over the X-rays (contacts appear white) from week 4 for each subject. The labels on the left mark the dorsal root exiting at that level. The approximate location of the spinal cord and the roots is also shown in yellow overlay. For scale, each contact is 3 mm long. (FIG. 6B) Weekly migration of the rostral tip of each of the leads for the three subjects (blue, red, yellow and purple circles for Subjects 1-4, respectively). For week 1, the comparison was between the weekly X-ray and the intraoperative fluoroscopic image. For subsequent weeks, the comparison was done between the weekly X-ray and the one from the preceding week. Median migrations are shown (solid lines). The X-ray for Subject 2 was taken from week 2, before leads were explanted.

FIGS. 8A-8C. Touchscreen interface for describing evoked sensory percepts. (FIG. 8A) Panel for free hand drawing to show the location and extent of the sensory percept. (FIG. 8B) and (FIG. 8C) Questionnaire to describe the modality of the sensory percept and associated phantom limb pain, if any.

FIG. 13 shows a set of diagrams illustrating the location of evoked sensations in response to activation of the implanted electrodes in Subject 4.

FIG. 14 is a graph showing results of McGill Pain Score evaluations of Subjects 1-4 treated for phantom limb pain by stimulation of dorsal rootlets and adjacent lateral spinal cord of sensory neurons innervating the amputated limb.

DETAILED DESCRIPTION

Introduction

Figure 1:
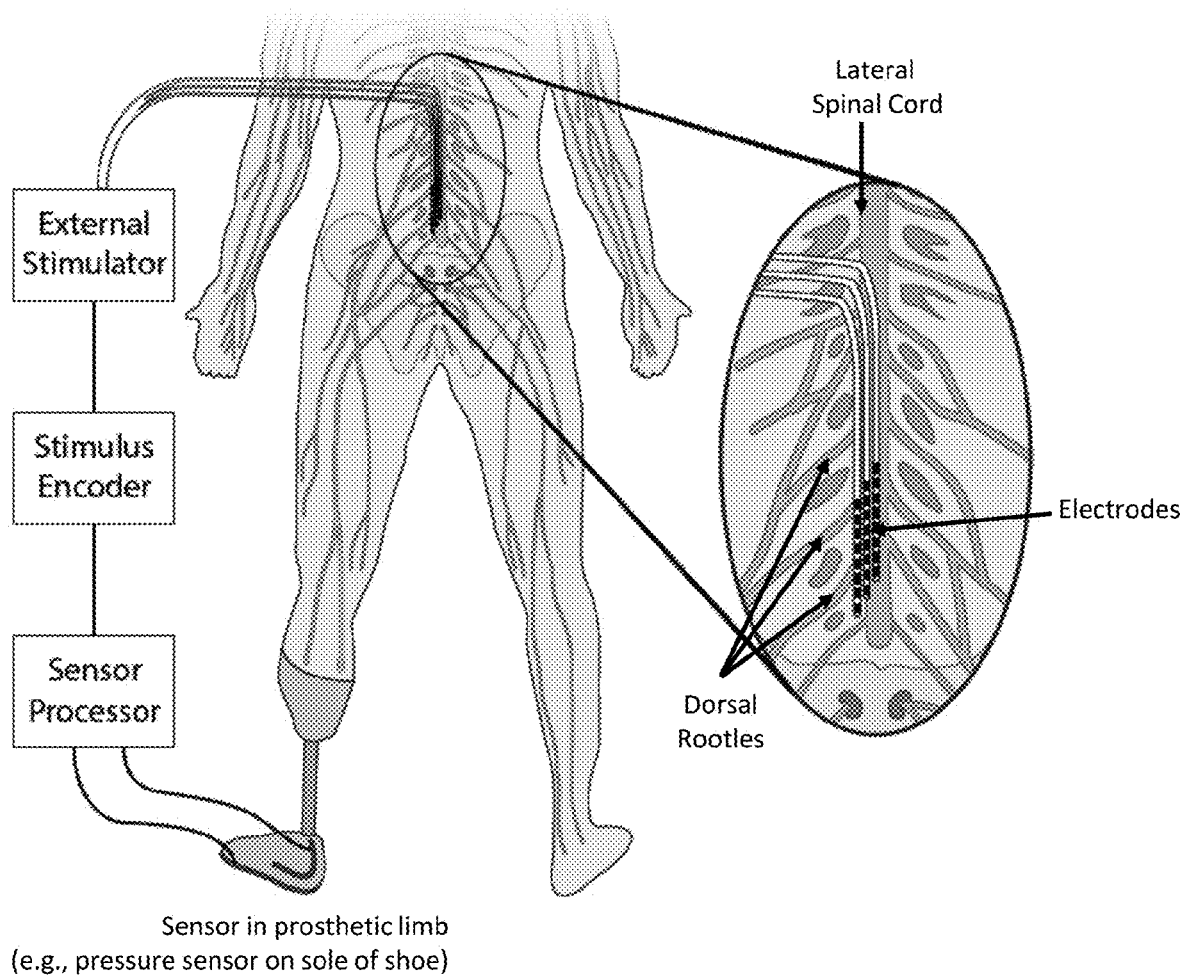
FIG. 1. Schematic illustration of aspects a non-limiting example of the method of treating phantom limb pain provided herein. As shown, a subject with a lower limb prosthesis and corresponding phantom limb pain is implanted with a neurostimulator that targets dorsal rootles and the lateral spinal cord adjacent to the dorsal rootles of sensory neurons innervating the limb with the phantom limb pain. The subject wears a prosthetic lower leg with a shoe that includes a pressure sensor in the sole or glove that includes a pressure sensor at the fingertip. Alternatively, the pressure sensor can be located at a corresponding location in the prosthetic. Activation of the pressure sensor in the sole of the shoe of the fingertip is detected by a sensor processor that sends signals to the stimulus encoder and stimulator of a neurostimulator connected to the electrodes implanted in the subject, which then stimulate the corresponding dorsal rootles and lateral spinal cord. Thus, activation of the pressure sensor activates the neurostimulator to activate the sensory neurons innervating the amputated limb. This activation pathway reduces the phantom limb pain in the subject. The depicted example shows an external stimulator and stimulus encoder, but internal devices may also be used.

Provided herein is a method of treating phantom limb pain and diabetic neuropathy pain by electrical stimulation of the dorsal spinal rootlets and the lateral spinal cord in subjects suffering from such pain. By modulating stimulation parameters (e.g. stimulus amplitude, pulse width, frequency), sensations are produced that appear to emanate from regions of the distal limb and feel natural. The stimulation is elicited in response to activation of one or more sensors that detect movement and/or position of the affected limb of the subject. As described herein, in individuals with amputation or peripheral neuropathy, this sensor-induced stimulation reduces phantom limb pain and diabetic neuropathy pain.

As described in more detail herein, these effects may be achieved by various stimulation parameters, including constant trains of stimulus pulses, trains that are modulated with functions such as sinusoids, or trains that mimic the natural firing patterns of sensory afferent neurons. Targeting the dorsal rootlets and the lateral spinal cord may be achieved using commercially available, FDA approved spinal cord stimulators targeted laterally in the epidural space, or through the use of more complex devices with a higher density of electrode contacts and shapes and sizes that better conform to the anatomical target.

Prior spinal cord stimulation systems target the dorsal columns, which are midline structures on the dorsal side of the spinal cord, with stimulation parameters that result in paresthesia (electrical buzzing sensation) to reduce pain in the desired anatomical location (depending on placement of the stimulator). These approaches are substantially different from the method provided herein, which relies on adjusting parameters based on signals recorded from the limbs (e.g. pressure at the fingertips or under the sole of the foot) and generated naturalistic sensations of touch, pressure, and joint movement to reduce phantom limb pain and diabetic neuropathy pain without producing paresthesia. This more naturalistic sensation is more comfortable to patients and may improve adoption and use of electrical stimulation devices for treatment of pain.

As discussed in more detail herein, sensor-induced electrical stimulation of the dorsal spinal rootlets and the lateral spinal cord can also be used to increase control of a prosthetic limb in an amputee. Unlike the method provided herein, prior stimulation systems that have also been assessed for restoration of sensory function and motor control in the upper- or lower-limbs after limb amputation rely on electrical stimulation of peripheral nerves in the residual limb.

DESCRIPTION OF TERMS

Unless otherwise noted, technical terms are used according to conventional usage. As used herein, the term "comprises" means "includes." Although many methods and materials similar or equivalent to those described herein can be used, particular suitable methods and materials are described below. In addition, the materials, methods, and examples are illustrative only and not intended to be limiting. The scope of the claims should not be limited to those features exemplified. To facilitate review of the various embodiments, the following explanations of terms are provided:

Diabetic neuropathy pain: An unpleasant sensory experience in a limb with a peripheral neuropathy due to complications of diabetes in a subject. Diabetic neuropathy is a type of nerve damage in a peripheral nerve caused by high blood sugar over long periods of time. Typically, nerves of the feet and legs are affected first, followed by nerves in the hands and arms. Typical symptoms of pain associated with a diabetic peripheral neuropathy include burning sensations, sharp pains, cramps, and "pins and needles" sensations.

Dorsal rootlets: A small branch of a root of a sensory neuron that emerges from the posterior spinal cord and travels to the dorsal root ganglion.

Electrode: An electric conductor through which an electric current can pass. An electrode can also be a collector and/or emitter of an electric current. In some embodiments, an electrode is a solid and comprises a conducting metal as the conductive layer. Non-limiting examples of conducting metals include noble metals and alloys, such as stainless steel and tungsten. An array of electrodes refers to a device with at least two electrodes formed in any pattern. A multi-channel electrode includes multiple conductive surfaces that can independently activated to stimulate or record electrical current.

Implanting: Completely or partially placing a neurostimulator or device including a neurostimulator within a subject, for example, using surgical techniques. A device or neurostimulator is partially implanted when some of the device or neurostimulator reaches, or extends to the outside of, a subject. A neurostimulator or device can be implanted for varying durations, such as for a short-term duration (e.g., one or two days or less) or for long-term or chronic duration (e.g., one month or more).

Lateral spinal cord: A region on the exterior surface of the spinal cord located between the dorsal midline and the point of entry of the dorsal rootlets into the main cord.

Neural signal: An electrical signal originating in the nervous system of a subject. "Stimulating a neural signal" refers to application of an electrical current to the neural tissue of a subject in such a way as to cause neurons in the subject to produce an electrical signal (e.g., an action potential). An extracellular electrical signal can, however, originate in a cell, such as one or more neural cells. An extracellular electrical signal is contrasted with an intracellular electrical signal, which originates, and remains, in a cell. An extracellular electrical signal can comprise a collection of extracellular electrical signals generated by one or more cells.

Neurostimulator: A medical device including one or more electrodes that can be placed in electrical contact with neuronal tissue and can stimulate neural signals in the neuronal tissue. Neurostimulators typically include electrodes with conductive and non-conductive surfaces designed for contact with neuronal tissue when implanted in a subject, and can include one or more electrodes that can be independently monitored from other conductive surfaces on or off the neurostimulator for stimulating neural signals. The electrodes are linked to a stimulator suitably designed for application of various current, voltage, pulse rate, waveforms etc., for generating a neural signal in one or more neurons in proximity to the electrode or electrodes included on the device. The linkage can be by way of one or more leads, although any operable linkage capable of transmitting electrical signal from the stimulator to the electrodes may be used. The stimulator can be placed internally or externally with regard to the patient. In several embodiments, a neurostimulator for use in the disclosed methods is a pulse generator.

Phantom limb pain: An unpleasant sensory experience perceived by a subject in an amputated limb (or portion thereof) of the subject. Phantom limb pain may occur at any time after amputation, such as within the first six months following amputation, or at later times. Typical symptoms of phantom limb pain include burning sensations, sharp pains, stabbing or shooting pains, cramps, and "pins and needles" sensations. Phantom limb pain is often unresponsive to first-line treatments and can result in sleep difficulties, loss of appetite, inability to focus, impaired personal hygiene, depression, and deterioration of interpersonal relationships.

Sensory neurons: Also known as afferent neurons, sensory neurons are nerve cells within the peripheral nervous system responsible for converting stimuli from the environment of the neuron into internal electrical impulses and transmitting the impulse to the central nervous system.

Subject: Living multi-cellular vertebrate organisms, a category that includes human and non-human mammals, including non-human primates, rats, mice, guinea pigs, cats, dogs, cows, horses, and the like. Thus, the term "subject" includes both human and veterinary subjects.

Therapeutically effective amount: An amount sufficient to provide a beneficial, or therapeutic, effect to a subject or a given percentage of subjects. Therapeutically effective amounts of a therapeutic treatment can be determined in many different ways, such as assaying for a reduction in a disease or condition (such as phantom limb pain). Therapeutic agents and treatments can be administered in a single dose, or in several doses, for example daily, during a course of treatment. However, the effective amount can be dependent on the source applied, the subject being treated, the severity and type of the condition being treated, and the manner of administration.

Treating or treatment: With respect to disease or condition (e.g., phantom limb pain), either term includes (1) preventing the disease or condition, e.g., causing the clinical symptoms of the disease or condition not to develop in a subject that may be exposed to or predisposed to the disease or condition but does not yet experience or display symptoms of the disease or condition, (2) inhibiting the disease or condition, e.g., arresting the development of the disease or condition or its clinical symptoms, or (3) relieving the disease or condition, e.g., causing regression of the disease or condition or its clinical symptoms.

Treating Phantom Limb Pain and Diabetic Neuropathy Pain

Provided herein is a method of treating phantom limb pain and diabetic neuropathy pain in a subject with or at risk of such pain. The method comprises providing a therapeutically effective amount of stimulation to dorsal rootlets, or lateral spinal cord adjacent to the dorsal rootlets, of sensory neurons innervating a limb of the subject with the phantom limb pain or the diabetic neuropathy pain. The stimulation is provided with one or more electrodes of a neurostimulator that are implanted at the dorsal rootlets or the lateral spinal cord adjacent to the dorsal rootlets in the subject. The one or more electrodes are activated to provide the stimulation in response to activation of a sensor detecting movement and/or position of the limb or movement and/or position of a physical or virtual prosthesis of the limb with the phantom limb pain or diabetic neuropathy pain. Coordination of the stimulation with the activation of the sensor treats the phantom limb pain or diabetic neuropathy pain in the subject.

A non-limiting mechanism for the onset of phantom limb pain and diabetic neuropathy pain is that the lack of afferent input in amputees or diabetic patients with peripheral neuropathy results in reductions in inhibitory exertion in the sensory transmission. In the descending pathway, inhibition is reduced in the periaqueductal grey and rostroventral medulla in the absence of the afferent input in patients with severed (or degraded) peripheral nerves. A response to the disinhibition impacts up regulation of channels in the periphery nerves and may lead to an increased activity in the dorsal neurons. The increased activity in the dorsal neurons may elicit phantom limb pain in amputees or diabetic neuropathy pain is diabetes patients with peripheral neuropathy. Thus, in some embodiments, targeting dorsal rootlets for stimulation using the method provided herein is believed to reduce phantom limb pain perception in amputees and neuropathy pain in diabetes patients with peripheral neuropathy.

FIG. 1 illustrates some aspects of a non-limiting example of the method herein. As shown, a subject with a prosthesis and phantom limb pain is implanted with a neurostimulator that targets dorsal rootlets and the lateral spinal cord adjacent to the dorsal rootlets of sensory neurons innervating the limb with the phantom limb pain (in this case, a leg with an amputated foot). The subject wears a prosthetic lower leg with a shoe that includes a pressure sensor in the sole. Activation of the pressure sensor in the sole of the shoe is detected by a sensor processor that sends signals to the stimulus encoder and stimulator of a neurostimulator connected to electrodes implanted in the subject, which then stimulate the dorsal rootlets and lateral spinal cord. Thus, activation of the pressure sensor in the sole of the shoe activates the neurostimulator to activate the sensory neurons innervating the amputated limb. The depicted example shows an external stimulator and stimulus encoder, but internal devices may also be used. This activation pathway reduces the phantom limb pain the subject. As discussed in more detail below, in several embodiments, the neurostimulator is calibrated to induce sensations of pressure, touch, joint movement, proprioception, and/or kinesthesia in the amputated limb in response to sensor-induced activation.

In another embodiment, a subject with an upper limb prosthesis and phantom limb pain is implanted with a neurostimulator that targets dorsal rootlets and the lateral spinal cord adjacent to the dorsal rootlets of sensory neurons innervating the upper limb with the phantom limb pain. The upper limb prosthesis includes a pressure sensor embedded at a suitable location in the prosthesis or in a covering of the prosthesis. For example the pressure sensor may be embedded in a finger of a prosthetic hand or in a glove covering the prosthetic hand. Activation of the pressure sensor is detected by a sensor processor that sends signals to the stimulus encoder and stimulator of a neurostimulator connected to electrodes implanted in the subject, which then stimulate the dorsal rootlets and lateral spinal cord. Thus, activation of the pressure sensor activates the neurostimulator to activate the sensory neurons innervating the amputated limb. An external or internal stimulator and encoder may be used. This activation pathway reduces the phantom limb pain the subject. As discussed in more detail below, in several embodiments, the neurostimulator is calibrated to induce sensations of pressure, touch, joint movement, proprioception, and/or kinesthesia in the amputated limb in response to sensor-induced activation.

Any appropriate subject with phantom limb pain or diabetic neuropathy pain can be treated with the method provided herein.

In some embodiments, the subject has diabetic neuropathy pain in a limb of the upper body, such as a hand or arm, or in a limb of the lower body, such as a foot or leg. Typical symptoms of diabetic neuropathy include numbness or reduced ability to feel pain or temperature changes, tingling or burning sensation, sharp pains or cramps, increased sensitivity to touch, muscle weakness, loss of reflexes, loss of balance and coordination, and serious foot problems such as ulcers, infections, and bone and joint pain. Often, patients experience diabetic neuropathy pain in the feet and legs first, followed by hands and arms. In some embodiments, the method further comprises selecting the subject with diabetic neuropathy pain for treatment.

In some embodiments, the subject has phantom limb pain in an amputated limb of the upper body, such as a hand or arm, or in an amputated limb of the lower body, such as a foot or leg. Typical phantom limb pain symptoms include burning sensations, sharp pains, stabbing or shooting pains, cramps, and "pins and needles" sensations, and can result in sleep difficulties, loss of appetite, inability to focus, impaired personal hygiene, depression, deterioration of interpersonal relationships. In some embodiments, the method further comprises selecting the subject with phantom limb pain for treatment.

Treatment of the phantom limb pain or diabetic neuropathy pain is generally initiated after the onset of the pain in the subject, although preventative embodiments are also envisioned. When administered following onset of the phantom limb pain or diabetic neuropathy pain, the treatment can be initiated at any time after pain onset. Treatment initiated after the development of the pain in the subject may result in reducing the severity of the symptoms of the phantom limb pain or diabetic neuropathy pain, or completely removing the symptoms. In some embodiments, the method provided herein is implemented as soon as possible following limb amputation (or even before), so as to maximally arrest cortical changes subsequent to amputation.

In one aspect of the disclosure, the phantom limb pain or diabetic neuropathy pain in the treated subject is delayed, prevented, or reduced.

Treatment prior to the development of the condition, such as treatment at or near the time of amputation, or treatment in a subject with a type of amputation typically associated with phantom limb pain, or treatment in a subject with symptoms of diabetic neuropathy but without diabetic neuropathy pain, is referred to herein as treatment of a subject that is "at risk" of developing the condition. In some embodiments, the treatment method can be performed during or after the occurrence of the conditions described herein.

In some embodiments, the method provided herein reduces the level of phantom limb pain or diabetic neuropathy pain in the subject by at least 20% (such as at least 30%, at least 40%, at least 50%, at least 60%, at least 70%, at least 80%, at least 90%) relative to before the treatment as measured by any appropriate pain evaluation. In some embodiments, the method provided herein reduce the level of phantom limb pain or diabetic neuropathy pain in the subject by at least 20% (such as at least 30%, at least 40%, at least 50%, at least 60%, at least 70%, at least 80%, at least 90%) relative to before the treatment as measured based on the McGill pain score. In some embodiments, the decrease in pain may result after the first week of treatment, and the pain may be reduced further in the following week, although alternate timeframes are also possible. Such decrease may be prolonged even after the removal of the neurostimulator from the subject.

The subject has one or more electrodes of a neurostimulator implanted at the dorsal rootlets, and/or the lateral spinal cord adjacent to the dorsal rootlets, of one or more sensory neurons innervating a limb of the subject with the phantom limb pain or the diabetic neuropathy pain. The electrodes are operably connected to a stimulator by any suitable means, such as by one or more leads.

Any neurostimulator suitable for stimulating the dorsal rootlets of one or more sensory neurons innervating a limb of a subject, and/or lateral spinal cord adjacent to the dorsal rootlets, can be used in the method provided herein. The neurostimulator includes a device for generating electrical current (the stimulator) connected to one or more electrodes suitable for conducting the current from the stimulator to the appropriate anatomical location in the subject. Typically, the stimulator is suitably designed for application of various current, voltage, pulse rate, waveforms etc., via the electrodes for generating neuronal activity in one or more neurons in proximity to the individual electrodes. In some embodiments, the neurostimulator is a pulse generator. In several embodiments, the neurostimulator is a commercially available FDA approved spinal cord stimulator placed in the epidural space. A more complex device with a higher density of electrode contacts and shapes and sizes that better conform to the anatomical target may also be implanted to function as a stimulator.

In several embodiments, the neurostimulator includes integrated circuitry to control the functions of the neurostimulator, including generation and application of electrical signals (via one or more channels of the electrodes implanted in the subject) to stimulate sensory neurons at the target location in the subject in response to activation of one or more sensors as described herein, as well as other. The integrated circuitry can comprise and/or be included within a controller (e.g., processor) for controlling the operations of the neurostimulator, including stimulating, signal transmission, charging and/or using energy from a battery for powering the various components of the device, and the like. Typically, the neurostimulator includes a pulse generator that provides stimulation energy in programmable patterns adapted for direct stimulation of sensory neurons at the dorsal rootlets and/or lateral spinal cord.

The electrodes of the neurostimulator can have any form appropriate for stimulating neural signals in the dorsal rootlets of one or more sensory neurons innervating a limb of a subject, and/or lateral spinal cord adjacent to the dorsal rootlets. In some embodiments, multi-channel electrodes are used. For example, the individual channels of the electrode can be calibrated to generate neural signals at a desired location in the subject (such as neural signals that induce sensations of pressure, touch, or joint movement at the location of the phantom limb pain or the diabetic neuropathy pain in the subject).

The electrodes of the neurostimulator are implanted in the subject within a suitable distance of the dorsal rootlets and/or lateral spinal cord of one or more sensory neurons innervating a limb of the subject with the phantom limb pain or the diabetic neuropathy pain. In some embodiments, the electrodes are located in the epidural space above the dorsal rootlets of one or more sensory neurons innervating a limb of the subject with the phantom limb pain or the diabetic neuropathy pain. In some embodiments, the electrodes are located in the epidural space above the lateral spinal cord adjacent to the dorsal rootlets of one or more sensory neurons innervating a limb of the subject with the phantom limb pain or the diabetic neuropathy pain. In several embodiments, the electrodes are anchored into position to prevent or reduce migration, for example, by attachment to bony structures near the implantation site.

Figure 2:
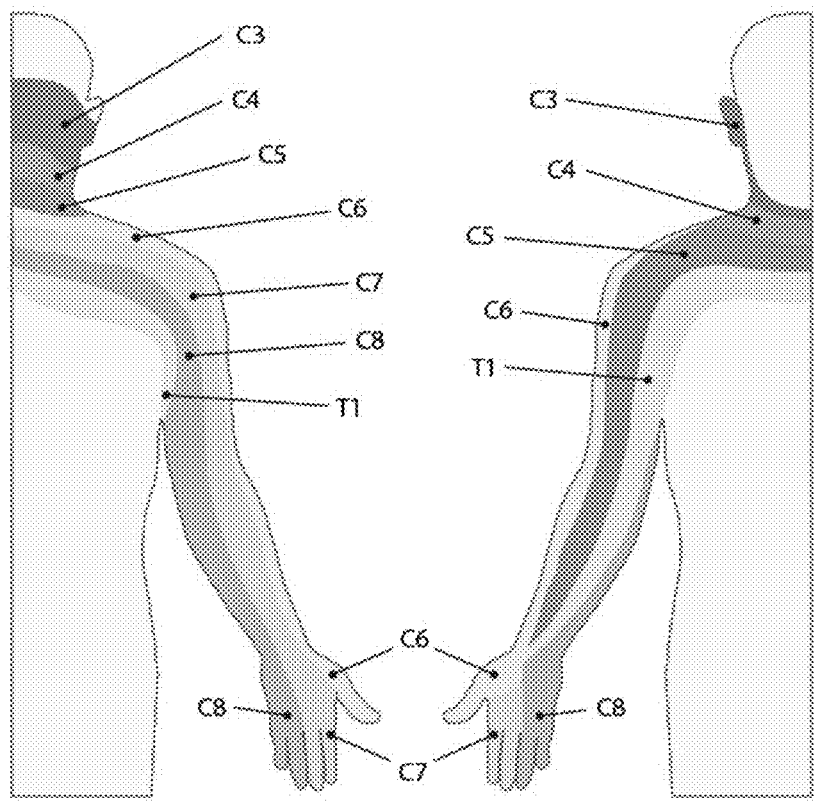
FIG. 2. Schematic illustration of sensory nerve targets in the upper and lower extremities.
Figure 2:
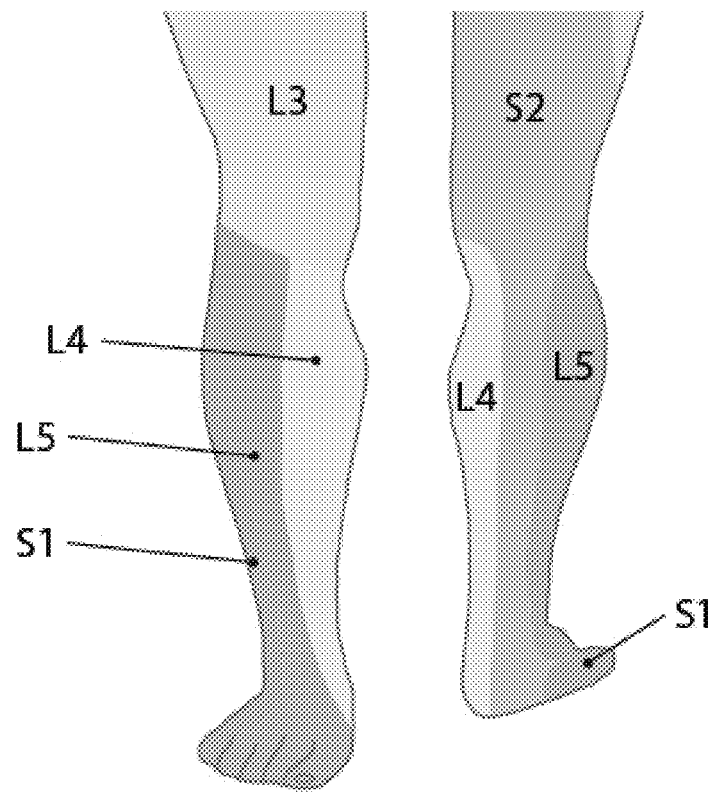

The electrodes can be implanted adjacent to the dorsal rootlets and/or lateral spinal cord at any appropriate position along the spinal cord, depending on the limb of the subject affected. FIG. 2 illustrates spinal positions that innervate particular anatomical areas. In some embodiments, the method is used to treat diabetic neuropathy pain or phantom limb pain in a lower extremity. Lumbar L2, L3, L4, L5, and/or sacral Si are known to contain sensory neurons receiving signals from the lower extremities and can be targeted for stimulation using the method provided herein. In some embodiments, the method is used to treat diabetic neuropathy pain or phantom limb pain in an upper extremity. Cervical DRG C3, C4, C5, C6, C7, thoracic DRG T1 are known to contain sensory neurons receiving signals from the upper extremities and can be targeted for stimulation using the method provided herein.

In some embodiments, the method further includes implanting the neurostimulator in the subject. Any appropriate method may be used to implant the electrodes of the neurostimulator at an appropriate anatomical location in the subject. In several embodiments, the electrodes of the neurostimulator are tunneled percutaneously and secured in place with tape or suture in the subject. The electrodes may be steered laterally under fluoroscopic guidance to target the dorsal rootlets and the lateral spinal cord, for example, using a stylet.

The implanted neurostimulator may remain in place for any suitable time period (such as about one month, about two months, about three months, about six months, about one year, or longer). In some embodiments, the electrodes remain implanted in the subject for the duration of time that the method provides a therapeutic benefit to the subject.

The one or more electrodes are activated to stimulate neural signals in the dorsal rootlets of one or more sensory neurons innervating a limb of a subject, and/or lateral spinal cord adjacent to the dorsal rootlets, in response to activation of a sensor detecting movement and/or position of the limb or movement and/or position of a physical or virtual prosthesis of the limb with the phantom limb pain or diabetic neuropathy pain. In several embodiments, when the subject moves the limb (or a prosthetic of the limb or portion thereof), this movement may be detected by a sensor capable of capturing such limb movement. The sensors may be placed at a suitable location to detect movements of the limb or prosthesis, for example, in a shoe or in a glove.

In embodiments involving a prosthetic limb (or portion thereof), any sensor suitable for detecting movement and/or position of the prosthetic may be used. The sensor may be located in or on the prosthetic, or in or on a stump of the limb to which the prosthetic is attached. In embodiments where the sensor is located in or on a limb of the subject (for example, in the case of a subject with diabetic neuropathy pain), any sensor suitable for detecting movement and/or position of the prosthetic may be used. Non-limiting examples of sensors for detecting movement of a limb or prosthetic limb include a gyroscope, an electrogoniometer, a textile piezoresistive sensor, or a pressure sensor located in or on the prosthesis, or in or on a limb, or stump of the limb to which the prosthetic is attached.

In some embodiments, the stimulation is applied in response to movement and/or position of a virtual prosthesis or limb with the phantom limb pain or diabetic neuropathy pain. The subject observes the virtual limb or prosthesis, the movement and/or position of which is used to trigger activation of the neurostimulator.

The applied stimulus parameters can vary depending on the particular subject and desired outcome. In several embodiments, the stimulus parameters are calibrated for the particular subject to be treated with the disclosed method.

In some embodiments, varying the electrical current patterns applied to the electrodes creates specific stimulation pattern to be delivered to the stimulation target. Non-limiting stimulation parameters that may be modulated include stimulus amplitude, pulse width, frequency, and duration in order to produce natural sensations in subjects. This may be achieved by providing recurring stimulation that mimic the natural firing patterns of sensory afferent neurons. These natural sensations may be effective in improvements with phantom limb pain. In some embodiments, recurring trains of stimulus pulses may be delivered to the anatomical targets. Further, the duration and frequency of stimulation can be varied as needed to optimize therapeutic outcome.

Any appropriate stimulation parameters can be used to stimulate to dorsal rootlets, or lateral spinal cord adjacent to the dorsal rootlets, of one or more sensory neurons innervating a limb of the subject with the phantom limb pain or the diabetic neuropathy pain. Non-limiting examples include a frequency of from 1-300 Hz (such as 10-50 Hz, 10-100 Hz, 10-200 Hz, 1-20 Hz, 1-30 Hz, 1-40 Hz, Hz, 1-50 Hz, 1-100 Hz, or 25-75 Hz, as well as frequencies in between these ranges), an amplitude of from 0.1-10 mA (such as 0.1-0.5 mA, 0.1-1 mA, 0.5-1 mA, 0.5-5 mA, 0.5-10 mA, 1-5 mA, 1-10 mA, or 5-10 mA, or an amplitude in between these ranges), a pulse duration of from 50-500 μsec (such as 50-100 μsec, 50-200 μsec, 50-300 μsec, 100-200 μsec, 100-300 μsec, 100-500 μsec, 200-500 μsec, or 300-500 μsec, or a pulse duration in between these ranges). In a non-limiting embodiment, the stimulation frequency is no more than 50 Hz. Additionally, the waveform used to stimulate the sensory neurons in the subject can have any appropriate form, such as a balanced biphasic square wave form.

In several embodiments, stimulation parameters are selected that elicit focal sensations of touch or pressure at the location of the phantom limb pain or diabetic neuropathy pain in the subject.

In some embodiments, the intensity of the stimulation (and resulting sensation) can be calibrated to correlate with the level of activity detected by the sensor detecting movement of the limb or movement of a physical or virtual prosthesis of the limb in the subject. For example, the stimulation parameters applied when the subject puts all their body weight on a prosthetic limb would elicit a more intense sensation of pressure or touch than when the subject places only part of their bodyweight on the prosthetic limb.

In several embodiments, stimulating the dorsal rootlets or the lateral spinal cord does not induce paresthesia in the limb with the phantom limb pain or diabetic neuropathy pain.

In some embodiments, a particular pattern of stimulation, which may be person-specific, will be more effective than others at treating phantom limb pain or diabetic neuropathy pain in the subject. In some embodiments, a pattern of signals approximating the train of signals received from a normal, innervated limb for communicating sensations of pressure, touch, or joint movement to the cortex is used. In some embodiments, the neurostimulator may be programmed to optimize such stimulation patterns, or the choice of stimulation patterns may be controlled by the subject or a health care provider. For example, subject or health care provider may adjust the amplitude and frequency of signals, for example, and also may select which channel (i.e., electrode) transmits which signal, to optimize signal pattern.

In several embodiments, the neurostimulator provides patterns of electrical stimulation to the dorsal rootles and lateral spinal cord that elicit pressure, touch, or joint movement sensations at the location of the phantom limb pain or diabetic neuropathy pain in the subject. For example, a microprocessor may be provided in conjunction with the neurostimulator that is programmed to accept signals produced by sensors in the prosthetic or virtual limb and transduce the signals to electrical signals sent via the implanted electrodes to the dorsal rootlets or lateral spinal cord adjacent to the dorsal rootlets. In some embodiments, signals from the sensor(s) in the prosthetic limb may be sent directly from a transmitter in the prosthetic limb to a receiver implanted in the subject and linked to the neurostimulator.

In several embodiments, the method further comprises calibrating the stimulation parameters applied to the dorsal rootlets of one or more sensory neurons innervating a limb of a subject, and/or lateral spinal cord adjacent to the dorsal rootlets, to induce sensations of pressure, touch, joint movement, proprioception, and/or kinesthesia at the location of the phantom limb pain or diabetic neuropathy pain in the subject. For example, in some embodiments, an amputee receives the sensation of a fingertip touching something if a touch sensor on a fingertip of the prosthetic limb is activated. In some embodiments, a microprocessor is included in or with the neurostimulator that can be programmed to facilitate this type of sensor-activated stimulation. It is believed that inducing such sensations in the limb of the subject with the phantom limb pain or the diabetic neuropathy pain leads to a superior reduction in such pain in the subject.

During calibration, subjects may be asked to report sensations experienced in response to the stimulation, and the stimulation parameters and/or electrode channels varied until the subject experiences sensations (such as sensations of pressure, touch, or joint movement) at the location of the phantom limb pain or diabetic neuropathy pain. Additionally, the intensity of the stimulation (and resulting sensation) can be calibrated to correlate with the level of activity detected by the sensor detecting movement of the limb or movement of a physical or virtual prosthesis of the limb in the subject. For example, the stimulation parameters applied when the subject puts all their body weight on a prosthetic limb would provide a more intense sensation of pressure or touch than when the subject places only part of their bodyweight on the prosthetic limb. Additionally, the subject can be evaluated for an overall level of phantom limb pain or diabetic neuropathy pain after each stimulus presentation or after a series of presentations. In a non-limiting embodiment, pain level is evaluated based on the McGill pain score.

Increasing Control of a Prosthetic Limb of a Subject

Also provided herein is a method of increasing control of a prosthetic limb of a subject. The method comprises providing a therapeutically effective amount of stimulation to dorsal rootlets, or lateral spinal cord adjacent to the dorsal rootlets, of sensory neurons innervating an amputated limb of the subject with a prosthesis. The stimulation is provided with one or more electrodes of a neurostimulator that are implanted at the dorsal rootlets or the lateral spinal cord adjacent to the dorsal rootlets in the subject. The one or more electrodes are activated to provide the stimulation in response to activation of a sensor detecting movement and/or position of the limb or movement the prosthesis or movement of a virtual prosthesis of the limb. Coordination of the stimulation with the activation of the sensor increases control of the prosthesis by the subject.

Any appropriate subject with a prosthetic limb can be treated with the method provided herein. The prosthetic can be an upper or lower body prosthetic, such as an above or below the elbow arm prosthetic, or an above or below the knee leg prosthetic.

The method can be in initiated at any time post-amputation to improve control of the prosthetic by the subject. In some embodiments, the method provided herein is implemented as soon as possible following limb amputation (or even before), so as to maximally arrest cortical changes subsequent to amputation.

In some embodiments, the method provided herein increases control of the prosthetic limb by the subject by at least 20% (such as at least 30%, at least 40%, at least 50%, at least 60%, at least 70%, at least 80%, at least 90%) relative to before the treatment as measured by any appropriate evaluation metric, such as a balance or strength metric (e.g., a sensory organization test).

In some embodiments, the method provided herein increases postural balance and stability by the subject by at least 20% (such as at least 30%, at least 40%, at least 50%, at least 60%, at least 70%, at least 80%, at least 90%) relative to before the treatment as measured by any appropriate evaluation metric, such as a balance or strength metric (e.g., a sensory organization test).

The subject has one or more electrodes of a neurostimulator as implanted at the dorsal rootlets, and/or the lateral spinal cord adjacent to the dorsal rootlets, of one or more sensory neurons innervating the limb of the subject with the prosthetic. The neurostimulator, electrodes, and target location of the electrodes used in the method of treating phantom limb pain as described herein can also be used in the disclosed method of increasing control of a prosthetic limb.

The one or more electrodes are activated to stimulate neural signals in the dorsal rootlets of one or more sensory neurons innervating a limb of a subject, and/or lateral spinal cord adjacent to the dorsal rootlets, in response to activation of a sensor detecting movement and/or position of a physical or virtual prosthesis of the amputated limb. In several embodiments, when the subject moves the limb (or a prosthetic of the limb or portion thereof), this movement may be detected by a sensor capable of capturing such limb movement. The sensors may be placed at a suitable location to detect movements of the limb or prosthesis, for example, in a shoe or in a glove.

Any sensor suitable for detecting movement and/or position of the prosthetic may be used. The sensor may be located in or on the prosthetic, or in or on a stump of the limb to which the prosthetic is attached. Non-limiting examples of sensors for detecting movement of a prosthetic limb include a gyroscope, an electrogoniometer, a textile piezoresistive sensor, or a pressure sensor located in or on the prosthesis, or in or on a stump of the limb to which the prosthetic is attached. In some embodiments, the stimulation is applied in response to movement of a virtual prosthesis or limb. The subject observes the virtual limb or prosthesis, the movement of which is used to trigger activation of the neurostimulator.

The applied stimulus parameters can vary depending the particular subject and desired outcome. In several embodiments, the stimulus parameters are calibrated for the particular subject to be treated with the disclosed method. In some embodiments, varying the electrical current pattern applied to the electrodes creates specific stimulation pattern to be delivered to the stimulation target. Stimulation parameters may be modulated including stimulus amplitude, pulse width, and frequency in order to produce natural sensations in subjects. This may be achieved by providing recurring stimulation that mimic the natural firing patterns of sensory afferent neurons. These natural sensations may be effective in increasing the control of the prosthetic limb by the subject. In some embodiments, recurring trains of stimulus pulses may be delivered to the anatomical targets. Further, the duration and frequency of stimulation can be varied as needed to optimize therapeutic outcome.

Any appropriate stimulation parameters can be used to stimulate to dorsal rootlets, or lateral spinal cord adjacent to the dorsal rootlets, of one or more sensory neurons innervating a limb of the subject with the prosthetic. Non-limiting examples include a frequency of from 1-300 Hz (such as 10-50 Hz, 10-100 Hz, 10-200 Hz, 1-20 Hz, 1-30 Hz, 1-40 Hz, Hz, 1-50 Hz, 1-100 Hz, or 25-75 Hz, as well as frequencies in between these ranges), an amplitude of from 0.1-10 mA (such as 0.1-0.5 mA, 0.1-1 mA, 0.5-1 mA, 0.5-5 mA, 0.5-10 mA, 1-5 mA, 1-10 mA, or 5-10 mA, or an amplitude in between these ranges), a pulse duration of from 50-500 μsec (such as 50-100 μsec, 50-200 μsec, 50-300 μsec, 100-200 μsec, 100-300 μsec, 100-500 μsec, 200-500 μsec, or 300-500 μsec, or a pulse duration in between these ranges).

In a non-limiting embodiment, the stimulation frequency is no more than 50 Hz. Additionally, the waveform used to stimulate the sensory neurons in the subject can have any appropriate form, such as a balanced biphasic square wave form.

In several embodiments, stimulation parameters are selected that elicit focal sensations of touch, pressure, joint movement, proprioception, and/or kinesthesia in the missing limb in the subject.

In some embodiments, the intensity of the stimulation (and resulting sensation) can be calibrated to correlate with the level of activity detected by the sensor detecting movement of the limb or movement of a physical or virtual prosthesis of the limb in the subject. For example, the stimulation parameters applied when the subject puts all their body weight on a prosthetic limb would elicit a more intense sensation of pressure or touch than when the subject places only part of their bodyweight on the prosthetic limb.

In several embodiments, stimulating the dorsal rootlets or the lateral spinal cord does not induce paresthesia in the amputated limb.

In some embodiments, a particular pattern of stimulation, which may be person-specific, will be more effective than others at increasing control of the prosthetic by the subject. In some embodiments, a pattern of signals approximating the train of signals received from a normal, innervated limb for communicating sensations of pressure, touch, joint movement, proprioception, and/or kinesthesia to the cortex is used. In some embodiments, the neurostimulator may be programmed to optimize such stimulation patterns, or the choice of stimulation patterns may be controlled by the subject or a health care provider. For example, subject or health care provider may adjust the amplitude and frequency of signals, for example, and also may select which channel (i.e., electrode) transmits which signal, to optimize signal pattern.

In several embodiments, the neurostimulator provides patterns of electrical stimulation to the dorsal rootles and lateral spinal cord that elicit pressure, touch, joint movement, proprioceptive, and/or kinesthetic sensations in the amputated limb. For example, a microprocessor may be provided in conjunction with the neurostimulator that is programmed to accept signals produced by sensors in the prosthetic or virtual limb and transduce the signals to electrical signals sent via the implanted electrodes to the dorsal rootlets or lateral spinal cord adjacent to the dorsal rootlets. In some embodiments, signals from the sensor(s) in the prosthetic limb may be sent directly from a transmitter in the prosthetic limb to a receiver implanted in the subject and linked to the neurostimulator.

In several embodiments, the method further comprises calibrating the stimulation parameters applied to the dorsal rootlets of one or more sensory neurons innervating a limb of a subject, and/or lateral spinal cord adjacent to the dorsal rootlets, to induce sensations of pressure, touch, joint movement, proprioception, and/or kinesthesia in the amputated limb. For example, in some embodiments, an amputee receives the sensation of a fingertip touching something if a touch sensor on a fingertip of the prosthetic limb is activated. In some embodiments, a microprocessor is included in or with the neurostimulator that can be programmed to facilitate this type of sensor-activated stimulation. It is believed that inducing such sensations in the amputated limb of the subject leads to a superior increase in control of a corresponding prosthetic.

During calibration, subjects may be asked to report sensations experienced in response to the stimulation, and the stimulation parameters and/or electrode channels varied until the subject experiences sensations (such as sensations of pressure, touch, joint movement, proprioception, and/or kinesthesia) in the amputated limb. Additionally, the intensity of the stimulation (and resulting sensation) can be calibrated to correlate with the level of activity detected by the sensor detecting movement of the limb or movement of a physical or virtual prosthesis of the limb in the subject. For example, the stimulation parameters applied when the subject puts all their body weight on a prosthetic limb would provide a more intense sensation of pressure or touch than when the subject places only part of their bodyweight on the prosthetic limb. Additionally, the subject can be evaluated for physical control of the prosthetic after each stimulus presentation or after a series of presentations using any suitable evaluation criteria, such as balance, dexterity, and/or strength.

EXAMPLES

The following examples are provided to illustrate particular features of certain embodiments, but the scope of the claims should not be limited to those features exemplified.

Example 1

Spinal Rootlet and Lateral Spinal Cord Stimulation to Improve Prosthesis Control and to Reduce Phantom Limb Pain in Upper-Limb Amputees This example illustrates the effectiveness of stimulating the spinal rootlets and the lateral spinal cord in upper-limb amputees to improve prosthesis control and to reduce phantom limb pain.

Restoring somatosensory feedback to people with limb amputations is crucial for improving prosthesis acceptance and function. Epidural spinal cord stimulation is a commonly used clinical procedure that targets sensory neural pathways in the dorsal spinal cord to treat pain conditions. A similar approach could be developed as a clinically translatable means to restore somatosensation in amputees. We show that epidural stimulation of the dorsal spinal cord evoked sensory percepts, perceived as emanating from the amputated arm and hand, in four people with upper-limb amputation. After an initial caudal movement immediately following the implantation, the leads stabilized, exhibiting a median migration of <5 mm (each electrode contact is 3 mm long) over the remainder of the study in all the subjects. This was reflected in the consistent locations of evoked percepts in the hand across four subjects throughout the period of implantation, which lasted up to 29 days. The median change in the centroid location was 1.2 to 35.3 mm and the median change in percept area was 0 to 40%. While most of the evoked percepts were paresthetic in nature, a subset was described as naturalistic (e.g. touch or pressure) in three subjects. Modulating the stimulus amplitude affected the perceived intensity of the sensation in all subjects. A variety of sensory percepts were evoked in all subjects irrespective of the level of amputation or the time since amputation, suggesting the approach is amenable to a diverse population of amputees.

Individuals with amputations consistently state that the lack of somatosensory feedback from their prosthetic device is a significant problem that limits its utility and is often a primary cause of prosthesis abandonment. In the case of upper-limb amputations, the absence of somatosensory feedback particularly affects the ability to generate the finely controlled movements that are required for object manipulation. Although sophisticated myoelectric prostheses with multiple degrees of freedom are becoming increasingly prevalent, their potential is limited because they provide little to no somatosensory feedback. In fact, body powered devices are often preferred by the users because of the feedback they provide through their harness and cable system. Addressing this limitation, cutting-edge robotic prosthetic arms have been designed with embedded sensors that could be harnessed for providing somatosensory feedback to the user. Thus, developing a robust and intuitive means of providing somatosensory feedback is an important endeavor to ensure the adoption and use of the latest advancements in prosthetics.

A variety of approaches have been explored to provide sensory feedback to amputees and examined the effects of feedback on prostheses control. Noninvasive devices, such as vibrotactors or surface electrodes, have been used to provide feedback via sensory substitution wherein an alternative modality replaces the one usually employed by the intact pathway (See, e.g., Patel et al., J Neural Engineering, 13(5):056015, 2016; Strbac et al., IEEE Transactions on Neural Systems and Rehabilitation Engineering, 25(11): 2133-2145, 11 2017; Štrbac et al.," J Neural Engineering, 13(4):046014, 2016; Witteveen et al., IEEE Transactions on Biomedical Engineering, 59(8):2219-2226, 2012; Raveh et al., Archives of Physical Medicine and Rehabilitation, 99(11):2263-2270, 2018). Because the sensations do not appear to emanate from the missing limb, sensory substitution may require significant learning for amputees to become adept in utilizing the feedback (Stepp et al., PLoS ONE, 7(2):e32743, 2 2012; Antfolk et al., IEEE Transactions on Neural Systems and Rehabilitation Engineering, 21(1):112-120, 1 2013). Somatotopically-matched feedback, wherein the user perceives the sensation at the contact location on the prostheses, may provide more intuitive signals (see, e.g., Zhang et al., J NeuroEngineering and Rehabilitation, 12:44, 12 2015; Chai et al., IEEE Transactions on Neural Systems and Rehabilitation Engineering, 25(5):469-480, 5 2017) for prosthetic control. Targeted sensory reinnervation is an approach that can allow vibrotactile or electrotactile feedback on the residual limb to be perceived as emanating from the missing limb (see, e.g., Marasco et al., Brain, 134(3): 747-758, 2011; Marasco et al., Brain, 132(Pt 6):1441-8, 2009). This is achieved by surgically redirecting the nerves that formerly innervated the missing limb to innervate patches of skin on the residual limb or elsewhere, and providing electrical or mechanical stimulation at the new innervation site (Kuiken et al., Lancet, 369(9559):371-380, 2007; Kuiken et al., PNAS, 104(50):20061-2006, 2007)). Additionally, sensory percepts have been evoked in the arm and hand by electrically stimulating neural pathways that remain intact post-injury (Dhillon and Horch. IEEE Transactions on Neural Systems and Rehabilitation Engineering, 13(4):468-472, 2005), including neural structures in both the peripheral (Horch et al., IEEE Transactions on Neural Systems and Rehabilitation Engineering, 19(5):483-489, 2011; Raspopovic et al., Science Translational Medicine, 6(222): 19-222, 2014; Tan et al., Science Translational Medicine, 6(257):138-257, 2014; Davis et al., J Neural Engineering, 13(3):036001, 2016) and central nervous systems (CNS) (Flesher et al., Science Translational Medicine, 8(361): 361ra141, 2016; Davis et al., Nature, 391(6665):385-387, 1 1998; Lee et al., Frontiers in systems neuroscience, 12:24, 2018; Johnson et al., Journal of Neural Engineering, 10(3): 036021, 6 2013). Peripheral nerves have been targeted using a variety of neural interfaces including epineural cuff electrodes like the flat interface nerve electrode (Tan et al., Science Translational Medicine, 6(257):138-257, 2014) or microelectrodes that penetrate the epineurium, such as the longitudinal intrafascicular electrode (Horch et al., IEEE Transactions on Neural Systems and Rehabilitation Engineering, 19(5):483-489, 2011), transverse intrafascicular multichannel electrode (Raspopovic et al., Science Translational Medicine, 6(222):19-222, 2014), or Utah slant array (Davis et al., J Neural Engineering, 13(3):036001, 2016). Approaches targeting the CNS in people with spinal cord injuries have used cortical surface electrodes and penetrating electrodes to stimulate cortical and thalamic regions of the brain to evoke sensations (Flesher et al., Science Translational Medicine, 8(361):361ra141, 2016; Davis et al., Nature, 391(6665):385-387, 1 1998; Lee et al., Frontiers in systems neuroscience, 12:24, 2018; Johnson et al., Journal of Neural Engineering, 10(3):036021, 6 2013). These approaches have clearly demonstrated the ability to evoke focal sensations that are perceived to emanate from the upper-limb, even decades after injury. However, they involve specialized electrodes and surgeries that are not part of common surgical practice. Further, the peripheral nerve approaches often target distal nerves, which could limit their use in people with proximal amputations such as shoulder disarticulations.

In this study, percutaneous SCS leads were implanted in four people with amputations and characterized the sensations evoked when the cervical spinal cord and spinal roots were stimulated. Subjects 1, 2, and 3 had above-elbow amputations while subject 4 had a transradial amputation. It was demonstrated that lateral SCS can evoke sensations perceived to emanate from the missing limb, including focal regions in the hand. These sensations were stable throughout the 29-day testing period and showed only minor changes in area and location. Additionally, in some cases, it was possible to evoke naturalistic, rather than paresthetic sensations. Finally, it was demonstrated that the intensity and modality of evoked percepts could be predicted with up to 90% accuracy based on the set of stimulation parameters (i.e. amplitude, frequency and pulse width) used, for each subject. This approach to sensory restoration could be one that is beneficial to a diverse population of amputees, including those with proximal amputations, and particularly amenable to clinical translation.

Materials and Methods

The aim of this study was to investigate whether electrical stimulation of lateral structures in the cervical spinal cord could evoke sensations that are consistently perceived to emanate from the missing hand and arm. It was also aimed to characterize those sensations and establish the relationship between stimulation parameters and the perceptual quality of evoked sensory percepts. Four subjects with upper-limb amputations (three females, one male; Table 1) were recruited for this study. Three amputations were between the elbow and shoulder and one was below the elbow. The time since amputation ranged from 2 to 16 years. All procedures and experiments were approved by the University of Pittsburgh and Army Research Labs Institutional Review Boards and subjects provided informed consent before participation.

Electrode implantation. SCS leads were implanted through a minimally invasive, outpatient procedure performed under local anesthesia. With the subject in a prone position, three 8- or 16-contact SCS leads (Infinion, Boston Scientific) were percutaneously inserted into the epidural space on the dorsal side of the C5-C8 spinal cord through a 14-gauge Tuohy needle. Contacts were 3 mm long, with 1 mm inter-contact spacing. Leads were steered via a stylet under fluoroscopic guidance, and electrode placement was iteratively adjusted based on the subjects' report of the location of sensations evoked by intraoperative stimulation. The entire procedure usually took approximately 3-4 hours. The leads were maintained for up to 29 days and subsequently explanted, by gently pulling on the external portion of the lead. Subjects attended testing sessions 3-4 days per week during the implantation period. The testing sessions lasted up to a maximum of 8 hours. Lead location and migration were monitored via weekly coronal and sagittal X-rays throughout the duration of implant.

Neural stimulation. During testing sessions, stimulation was delivered using three 32-channel stimulators (Nano 2+Stim; Ripple, Inc.). The maximum current output for these stimulators was 1.5 mA per channel. In order to achieve the higher current amplitudes required for SCS, a custom-built circuit board was used to short together the output of groups of four channels, thereby increasing the maximum possible output to 6 mA per channel resulting in a total of 8 effective channels per stimulator. Custom adapters were used to connect each stimulator to 8 contacts on each of the implanted leads. Custom software in MATLAB was used to trigger and control stimulation. Stimulation pulse trains were charge balanced, cathodic-first square pulses, with either asymmetric or symmetric cathodic and anodic phases. For asymmetric pulses, the anodic phase was twice the duration and half the amplitude of the cathodic phase. Stimulation was performed either in a monopolar configuration, with the ground electrode placed at a distant location such as on the skin at the shoulder or hip, or in a multipolar configuration with one or more local SCS contacts acting as the return path. Stimulation frequencies and pulse widths ranged from 1-300 Hz and 50-1000 µs, respectively. The interphase interval was 60 µs. All stimulus amplitudes reported in this manuscript refer to the first phase amplitude.

Recording perceptual responses. The first few sessions of testing were primarily devoted to recording the location and perceptual quality of sensory percepts evoked with various stimulation configurations. An auditory cue was provided to denote the onset of stimulation. At the offset of each stimulation train, the subject used a touchscreen interface developed in Python (FIGS. 8A-8C) to document the location and perceptual quality of the evoked sensation. The location of the sensory percept was recorded by the subject using a free-hand drawing indicating the outline of the evoked percept on an image of the appropriate body segment, i.e., hand, arm or torso. The percept quality was recorded using several descriptors: mechanical (touch, pressure, or sharp), tingle (electrical, tickle, itch, or pins and needles), movement (vibration, movement across skin, or movement of body/limb/joint), temperature, pain due to stimulation, and phantom limb pain. Each descriptor had an associated scale ranging from 0-10 to record the corresponding perceived intensity. Additionally, the subject was instructed to rate the naturalness (0-10) and the depth of the perceived location of the percept (on or below the skin, or both). This set of descriptors have been used previously to characterize evoked sensory percepts (see Lenz et al., J neurophysiology, 70(1):200-12, 7 1993; and Heming et al., J Neural Engineering, 7(6), 2010).

Analyzing sensory percept distribution. The spinal cord segment targeted by stimulation through each electrode was inferred from the X-ray images. The pedicles of each vertebra were used to mark the boundaries that separated each spinal root. Any electrode located within these boundaries was assumed to preferentially stimulate the nearest spinal root. Similarly, boundaries were drawn on the body segment outline images to divide them into 7 anatomical segments (FIG. 4A) including thumb, D2-D3, D4-D5, wrist, forearm, elbow, and upper arm. The sensory percepts were categorized as being associated with one of the seven anatomical segments based on which segment contained the maximal area of the perceived sensation. For this analysis, only those sensory percepts that were evoked ipsilateral to the amputation were included, since bilateral and contralateral sensations would not be useful for neuroprosthetic applications. Dermatome maps were generated per subject, by determining the proportion of electrodes situated at each spinal level that evoked a sensation in a specific anatomical region.

Figure 6A:
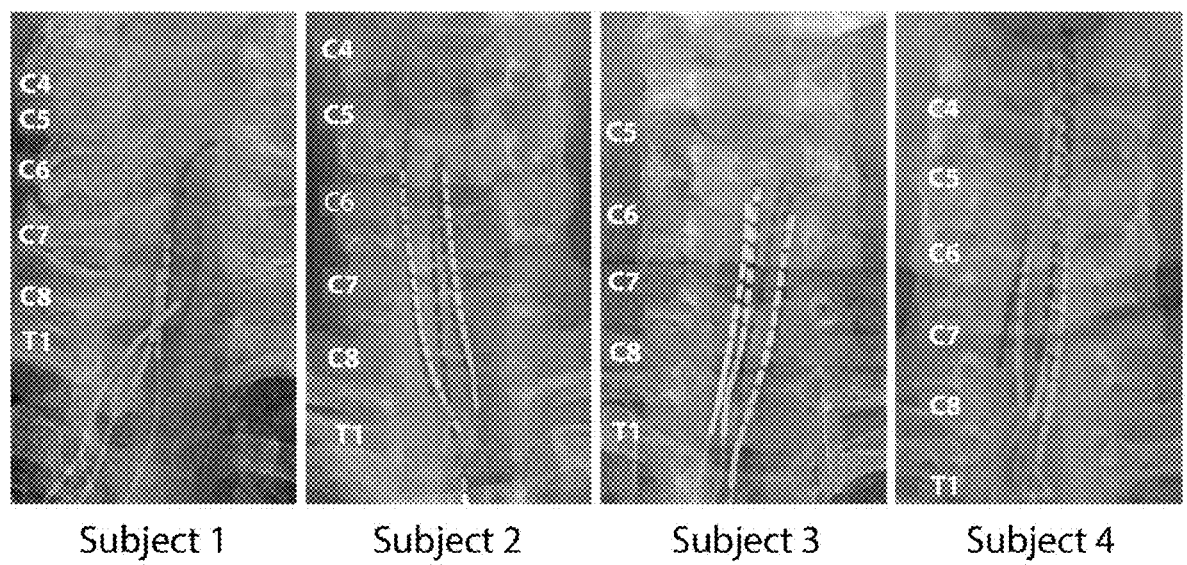
FIGS. 6A-6B. Stability of the SCS leads after implantation.

Quantifying lead and percept migration. The intraoperative fluoroscopy image, superimposed over the X-rays from the first and last week of testing, gave an indication of gross movements of the leads. Using bony landmarks, the X-ray from the first week was aligned to the intraoperative fluoroscopy image, and each subsequent X-ray was aligned to the X-ray from the previous week using an affine transformation method in MATLAB. The SCS contact that appeared to be most parallel to the plane of imaging was used to determine the scale length for the image (SCS contacts are 3 mm in length). For each lead, the distance between the rostral tips of the electrodes as seen in the aligned image pairs (FIGS. 6A and 6B) was measured to determine the rostro-caudal migration. Positive values signified caudal migration and negative values signified rostral migration. To quantify migration of perceived sensations, the change in the position of the centroid and the change in area of each percept that was localized to the hand was measured. For sensations that included a percept outside the hand, only the hand percept was used in these calculations, as this is the most relevant location for a somatosensory neuroprosthesis. The minimum stimulus amplitude that was tested at least once per week was selected for the highest number of weeks during the implant (minimum modal amplitude). The migration of these centroids with respect to the median location of the centroids for each electrode was quantified. The distances were converted to millimeters using the average hand length of 189 mm (as measured from the tip of the middle finger to the wrist) of a human male. Similarly, the area of each evoked percept in the hand was compared to the median area for each electrode and the difference was normalized to the total area of the hand. All electrodes that were tested in at least two of the weeks of implant were included in the analysis.

Detection thresholds. A two-alternative forced choice task was used to determine detection thresholds. The subject was instructed to focus on a fixation cross on a screen. Two 1s-long windows, separated by a variable delay period, were presented and indicated by a change in the color of the fixation cross. Stimulation was randomly assigned to one of the two windows. After the second of the two windows, the fixation cross disappeared, and the participant was asked to report which window contained the stimulus. The stimulus amplitude for each trial was varied using a threshold tracking method (See Leek, Perception & Psychophysics, 63(8): 1279-1292, 11 2001; Levitt, J Acoustical Society of America, 49(2B):467-477, 2 1971) with a 'one-up, three-down' design. In this design, an incorrect answer resulted in an increase in stimulus amplitude for the next trial while three consecutive correct trials were required before the stimulus amplitude was decreased. Stimulus amplitude was always changed by a factor of 2 dB. Five changes in direction of the stimulus amplitude, either increasing to decreasing or vice versa, signaled the end of the task. Using this task design, the detection threshold was determined online as the average of the last 10 trials before the fifth change in direction. A detection threshold calculated this way corresponds approximately to correctly identifying the window containing the stimulus 75% of the time (Garcia-Perez. Vision Research, 38(12):1861-1881, 1998). To get a better estimate of the detection threshold a psychometric curve was fit to the data post-hoc using the Palamedes toolbox and the detection threshold was calculated as the stimulus amplitude at the 75% accuracy level. Tasks in which accuracy levels for all stimulus amplitudes were <0.6 or >0.9 were omitted from this analysis. Thresholds calculated for the same electrodes on different days were averaged together to obtain a mean detection threshold for each electrode.

Just-noticeable differences. A similar two-alternative forced choice task was used to determine just-noticeable differences in amplitudes. The design of the task was identical to the detection task except stimulation was provided in both the windows and the subject was instructed to choose the window with higher perceived intensity of stimulation. One of the stimulation amplitudes in every trial was held constant while the other was chosen randomly from a list of stimulus amplitudes constituting a block. The constant amplitude was either fixed at 2.5 mA for the lower standard amplitude or at 4.0 mA for the higher standard amplitude. The windows in which standard and the test amplitude were administered was randomized as well. This block of stimulus amplitudes was repeated up to 8 times and the presentation sequence was randomized within each block. A psychometric curve was fit to the data post-hoc using the Palamedes toolbox and the JND was calculated as the stimulus amplitude at the 75% accuracy level. Tasks in which accuracy levels for all stimulus amplitudes were <0.6 or >0.9 were omitted from this analysis. JNDs calculated for the same standard amplitude on different electrodes for a given subject were averaged together to obtain a mean JND for each standard amplitude.

Perceived intensities of the evoked sensory percepts. A free magnitude estimation task was used to determine the relationship between stimulus amplitude and perceived intensity of the evoked sensations. In this task, subjects were instructed to rate the perceived intensity on an open-ended numerical scale as stimulation amplitude was varied randomly. A block of stimulus amplitudes consisted of 6-10 values linearly spaced between the detection threshold of the electrode being tested and the highest value that did not evoke a painful percept up to 6 mA. This block of chosen amplitudes was presented six times and the presentation sequence was randomized within each block. The subject was instructed to scale the response appropriately such that a doubling in perceived intensity was reported as a doubling in the numerical response. Zero was used to denote that no sensation was perceived in response to the stimulus. Data from the first block was not included in the analysis.

Statistical Analysis. SAS version 9.4 was used for the following analyses. A series of Generalized Linear Models (GLM) were created, which allowed the examination and testing of the statistical significance of the following: 1) effects of the stimulation parameters on the intensity of the evoked sensation for each categorical modality descriptor, and 2) effects of stimulation amplitude on the area and intensity of the evoked percept. In addition, we utilized a Naive Bayes classifier to predict the categorical descriptors for 'movement', 'mechanical', and 'tingle' from stimulation parameters, subject, and time since implant. This particular classification algorithm requires very little training, compared to other classification methods, and is preferable with small sample sizes. Confusion matrices were created to examine the proportion of correctly classified sensations. Separate auto-regressive time series models were created to examine the changes in distributions for both area and centroid distance over time, adjusting for autocorrelations in the data. The AUTOREG procedure in SAS estimates and forecasts linear regression models for time series data when the errors are autocorrelated or heteroscedastic. If the error term is autocorrelated (which occurs with time series data), the efficiency of ordinary least-squares (OLS) parameter estimates is adversely affected and standard error estimates are biased, thus the autoregressive error model corrects for serial correlation. For models with time-dependent regressors, the, AUTOREG procedure performs the Durbin t-test and the Durbin h-test for first-order autocorrelation and reports marginal significance levels.

Results

SCS evokes sensory percepts localized to the missing limb. Three SCS leads were implanted in the cervical epidural space in each of four individuals with upper-limb amputation (Table 1). The percutaneous implant was maintained for the full 29-day duration of the study for all subjects except subject 2, who requested removal of the leads after two weeks due to personal factors and discomfort from caudal migration of one of the leads. We stimulated in both monopolar as well as multipolar electrode configurations. Stimulus amplitudes, frequencies and pulse widths ranged from 0-6 mA, 1-300 Hz and 50-1000 µs, respectively.

TABLE 1

Demographic, amputation and study-related information for each subject.

| | | | Amputation characteristics | | | |
|---|---|---|---|---|---|---|
| Subject | Age | Gender | Years since | Side | Level | Cause | Implant Duration |
| 1 | 67 | Female | >5 | Right | Shoulder disarticulation | Necrotizing fasciitis | 29 days |
| 2 | 33 | Male | >16 | Left | Transhumeral | Trauma | 15 days |
| 3 | 38 | Female | >2 | Right | Transhumeral | Trauma | 29 days |
| 4 | 44 | Female | >3 | Right | Transradial | Compartment syndrome | 29 days |

Figure 3:
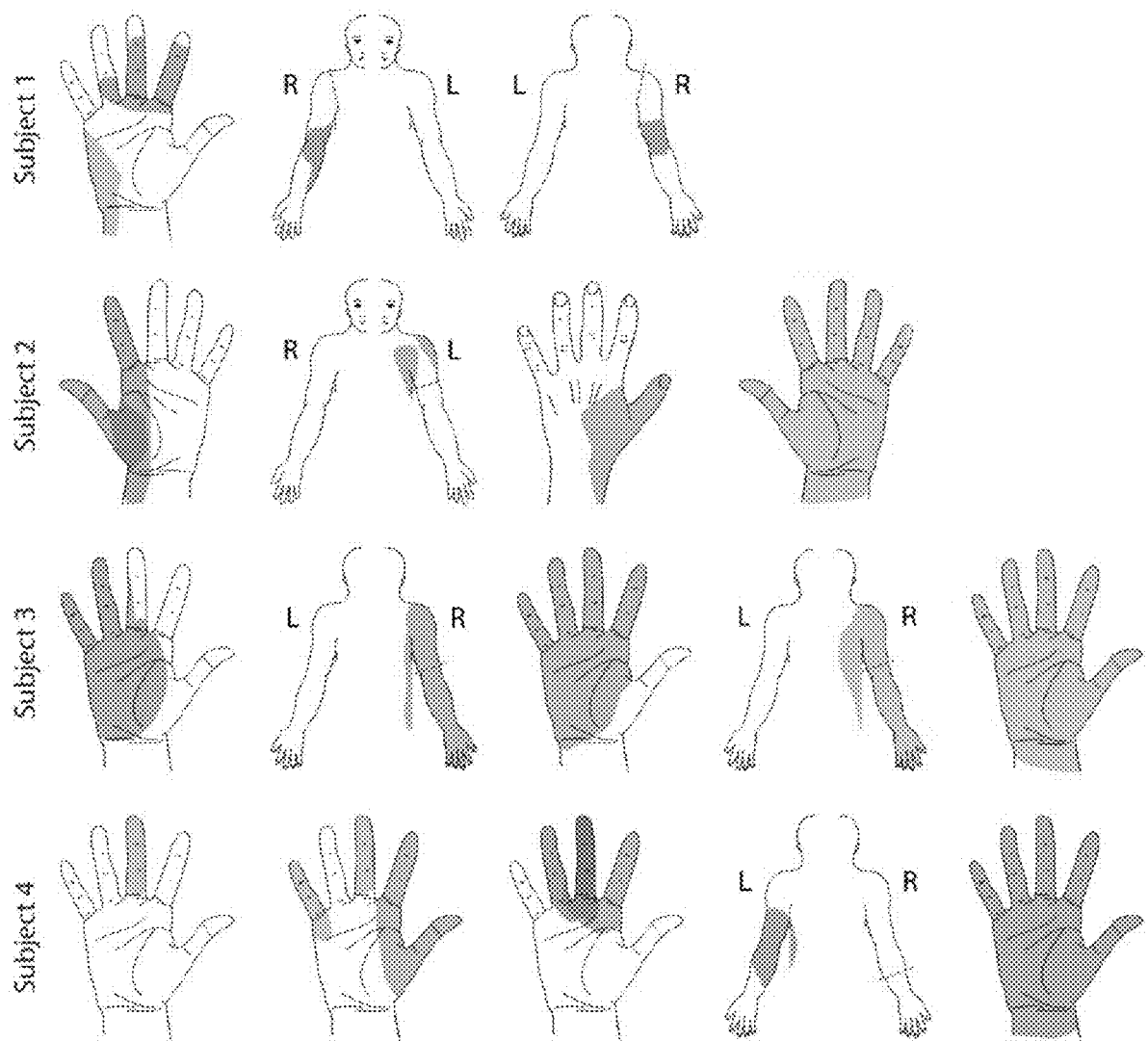
FIG. 3. Representative sensory percepts for Subjects 1-4. Colored areas represent the projected field for distinct evoked percept that were reported for more than 2 testing sessions and remained stable for at least 2 weeks. Each color represents a unique stimulation electrode per subject. Pairs of percepts with more than 70% overlap were excluded if there were percepts in the same location with lesser overlap (more local).
Figure 9:
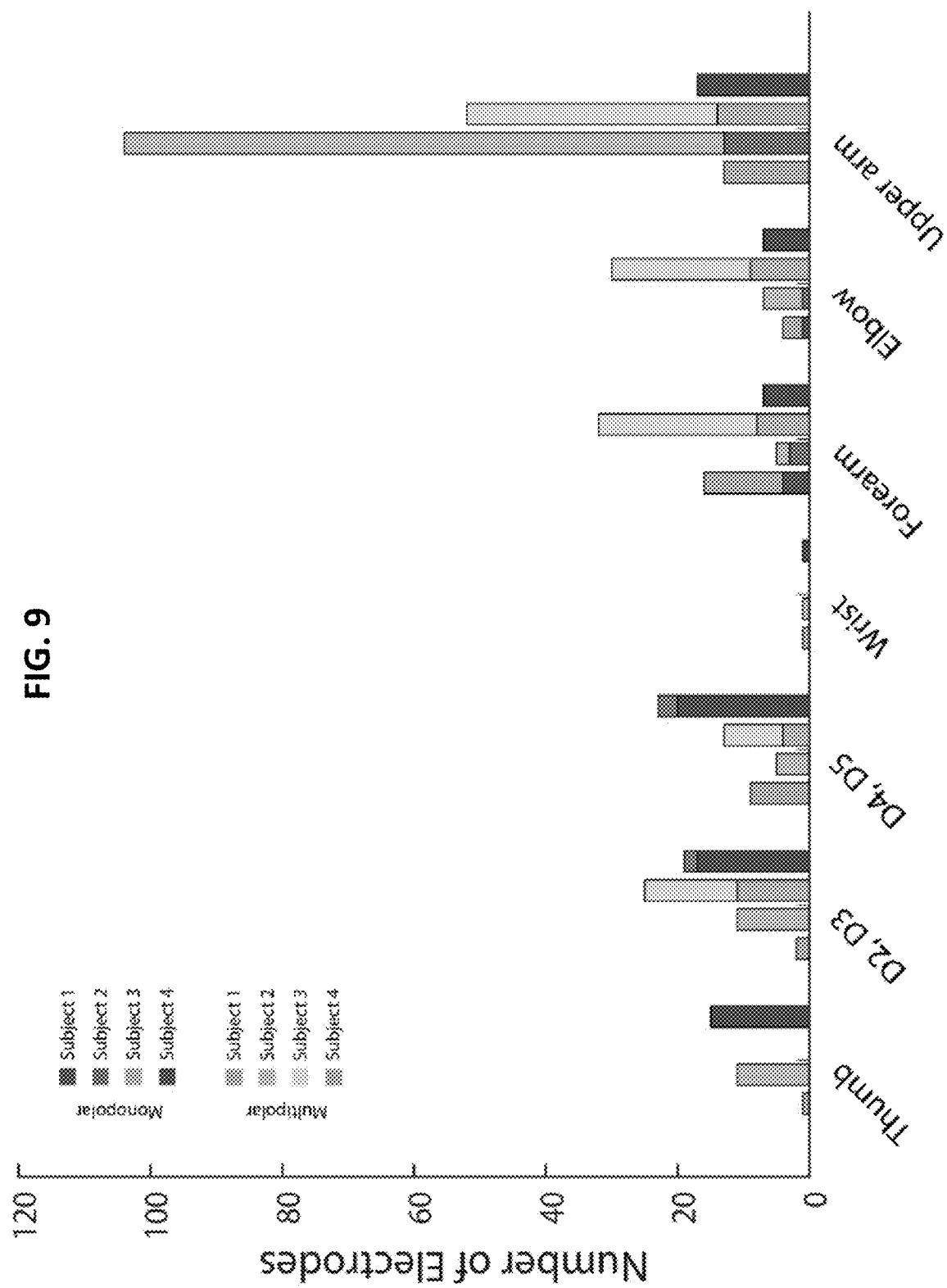
FIG. 9: Effect of monopolar and multipolar stimulation. The number of electrodes that evoked a sensory percept at a specific anatomical location. Lighter colored bars indicate monopolar electrodes and darker colored bars indicate multipolar electrodes in Subjects 1 (blue), 2 (red), 3 (yellow) and 4 (purple).

In all four subjects, epidural SCS evoked sensory percepts in distinct regions of the missing limb including the fingers, palm, and forearm. While some sensory percepts were diffuse and covered the entire missing limb, other percepts were localized to a very specific area, such as the ulnar region of the palm or wrist, or individual fingers. FIG. 3 shows representative responses in Subjects 1-4. In Subjects 1 and 2, only multipolar stimulation evoked sensory percepts that were localized to the focal regions of the missing limb (FIG. 9). In Subjects 2 and 3, most percepts were accompanied by a sensation on the residual limb. This was the case even when the primary percept was focally restricted to the distal regions of the missing limb. In subjects 1, 2, and 4 these additional sensations emanated predominantly from the end of the residual limb. The frequency of simultaneous percepts in the residual and phantom limb varied from subject to subject. At threshold, paired sensations (perceived in the hand and residual limb) occurred in 0%, 92%, 98% and 8% of all reported sensations for subjects 1-4 respectively.

Figures 4A, 4B:
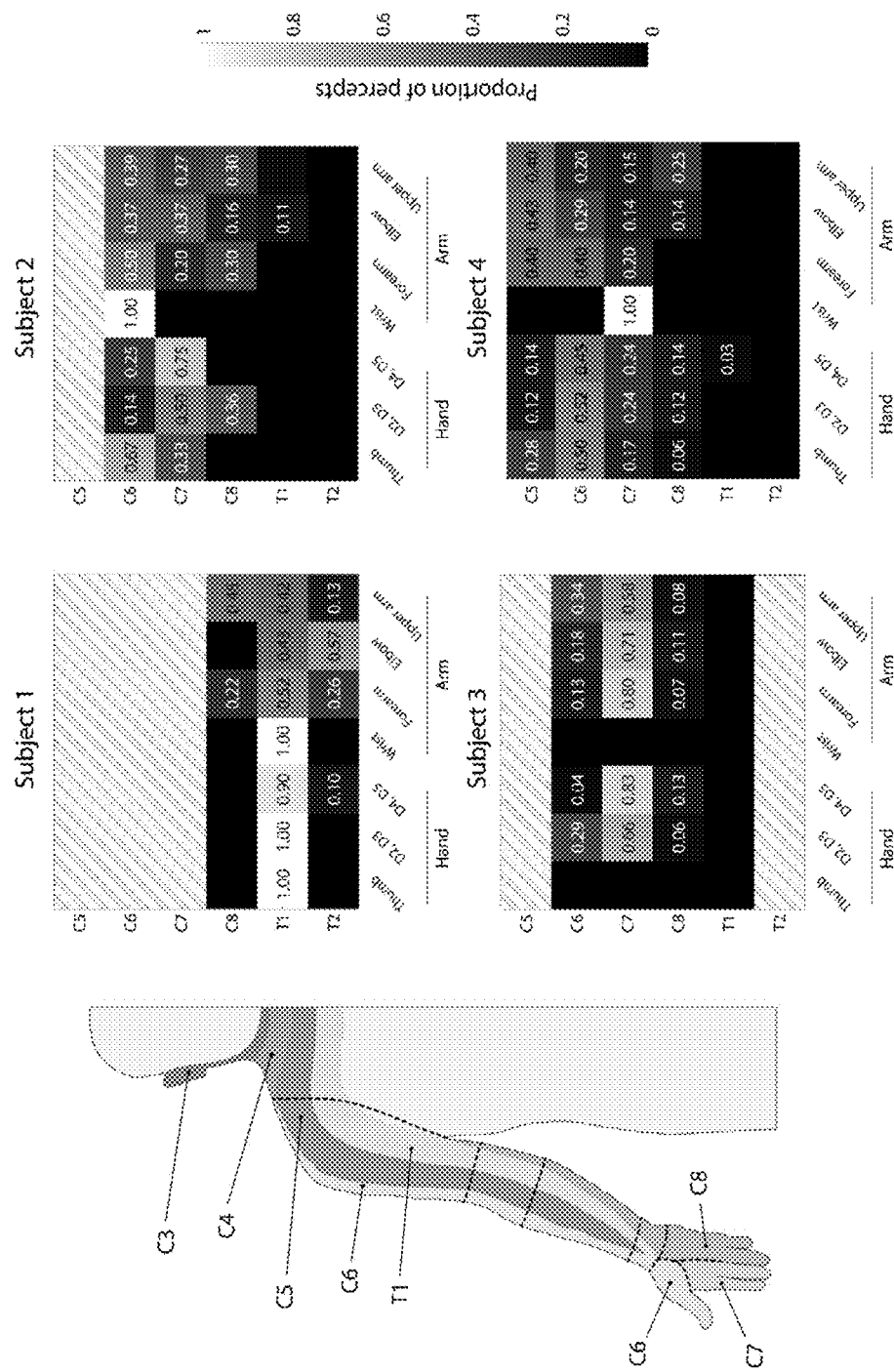
FIGS. 4A and 4B. Dermatomal organization of the evoked percepts.
Figure 10:
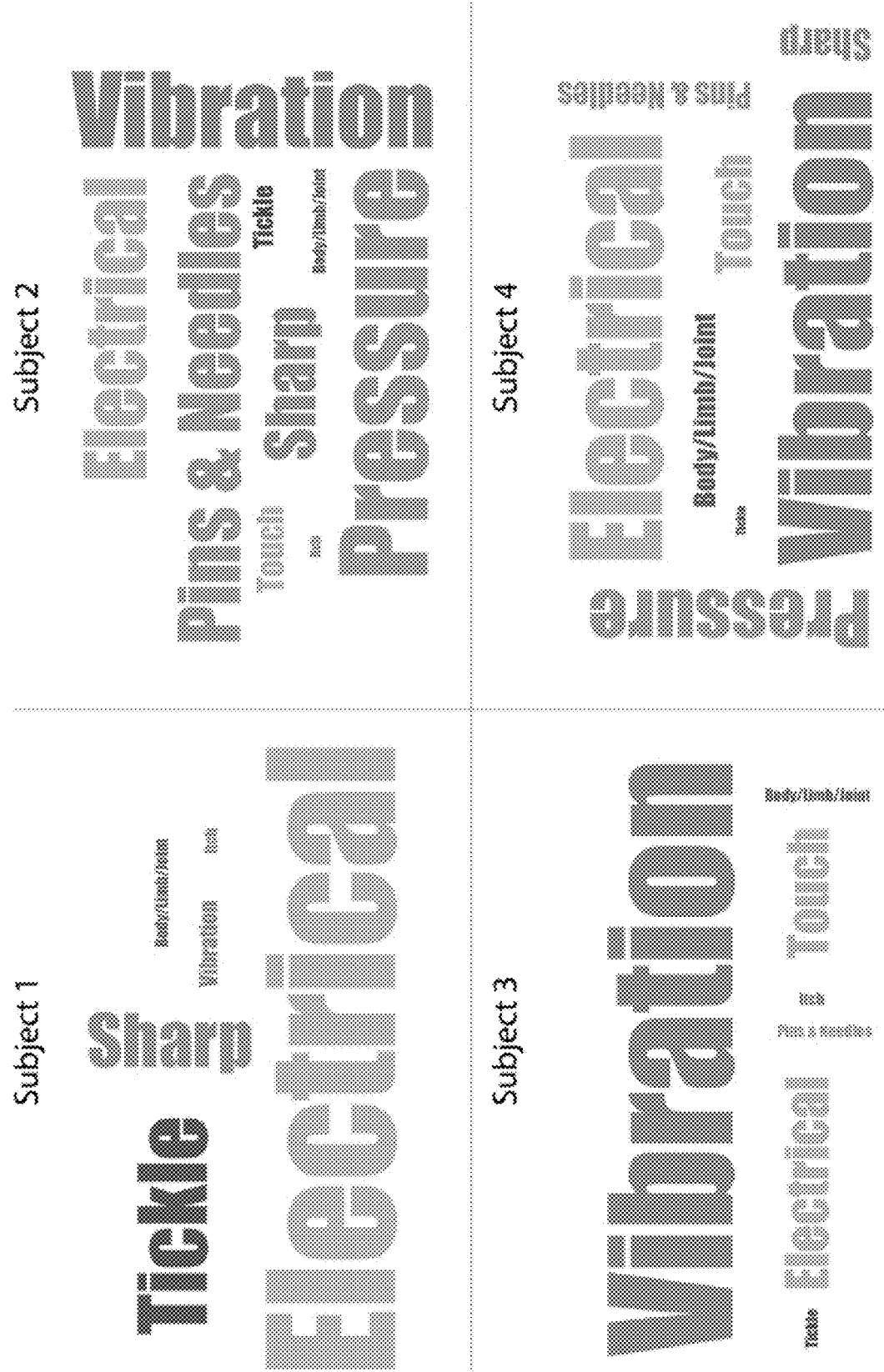
FIG. 10: Word cloud for all evoked percepts per subject. The size of each descriptor word is proportional to the number of times it was used to describe the mechanical, tingle and movement properties of the evoked percept. Table 2 contains a list of all descriptor words available to the subjects.

FIGS. 4A and 4B show the proportion of electrodes situated at each spinal level that evoked a sensation in a specific anatomical region. While there was considerable inter-subject variability, some notable similarities between these results and traditional dermatomes were observed. For example, sensations reported in the thumb were evoked by electrodes located near the C6 root (Subject 2: 67%, Subject 4: 50%). Similarly, a high proportion of the percepts localized to D2 and D3 were evoked by electrodes near the C7 root (Subject 2: 50%, Subject 3: 66%). In contrast, sensations in D4 and D5 (within the C8 dermatome) were evoked predominantly by electrodes near the C7 root (75% and 83% in Subjects 2 and 3, respectively). Interestingly, for subject 4 electrodes near the C6 root produced a majority of the percepts in the hand (D2-D3: 52%, D4-D5: 45%). Moreover, almost all the electrodes in Subject 1, including those that evoked focal percepts in the fingers and palm, were located near the T1 roots. The subjects were asked to describe the evoked sensations using a set of words provided from a predefined list (Table 2). This allowed us to standardize the descriptions of the percepts across subjects. A vast majority of the sensory percepts were described as "electrical tingle", "vibration," or "pins and needles", i.e. paresthesia (FIG. 10). Of all stimulation trials with a unique combination of stimulation parameters (i.e. electrode, amplitude, frequency and pulse width), evoked percepts were described as paresthetic in 96%, 92.3%, 75.6% and 98.3% for Subjects 1-4, respectively. More naturalistic modalities, like "touch" and "pressure", were elicited to varying degrees of success among the subjects (none in Subject 1; 78.6%, 29.6% and 83.1% of unique stimulation parameter combinations in Subjects 2-4, respectively). Subjects were allowed to report more than one modality simultaneously, and the touch-like sensations in Subject 2 and 4 were frequently accompanied by a simultaneous paresthetic sensation. Only 8.5% of the trials in Subject 2 evoked a touch or pressure percept alone. Percepts containing a dynamic ('movement') component that may be described as proprioceptive were evoked at least once in all subjects. Subjects were able to describe distinct sensations in the phantom such as opening and closing of the hand, movement of the thumb, and flexing of the elbow that occurred while stimulation was being delivered. These sensations could be evoked consistently over a span of minutes but, we were unable to evoke them reliably over longer time courses. As such, it is currently unlikely that they would be useful for a somatosensory neuroprosthesis.

TABLE 2

Descriptors provided for characterizing the evoked percepts. The various descriptors that subjects were asked to choose from while describing the modality and intensity of the evoked sensory percept. Visual analog scales (VAS) were presented as a slider bar and no specific numbers were shown.

| Naturalness | Depth | Mechanical | Tingle | Movement | Temperature |
|---|---|---|---|---|---|
| VAS (Totally Unnatural to Totally Natural) | Skin surface Below Skin Diffuse Both VAS (intensity) | Touch Pressure Sharp VAS (intensity) | Electrical Tickle Itch Pins & Needles VAS (intensity) | Vibration Body/limb/joint Across skin | VAS (Very Cold to Very Hot) |

Figure 5A:
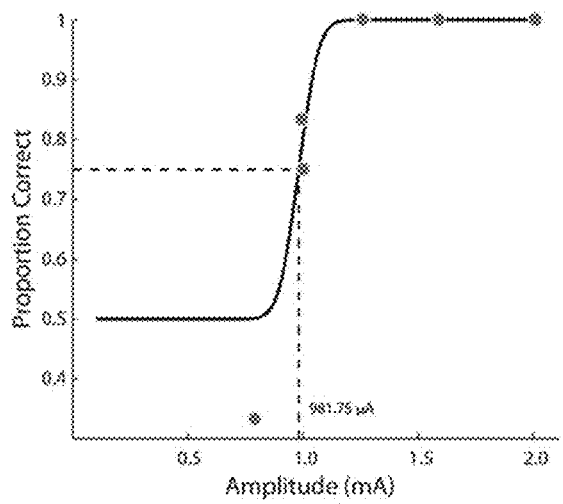
FIGS. 5A-5E. Psychophysics of the evoked sensory percepts.
Figure 5B:
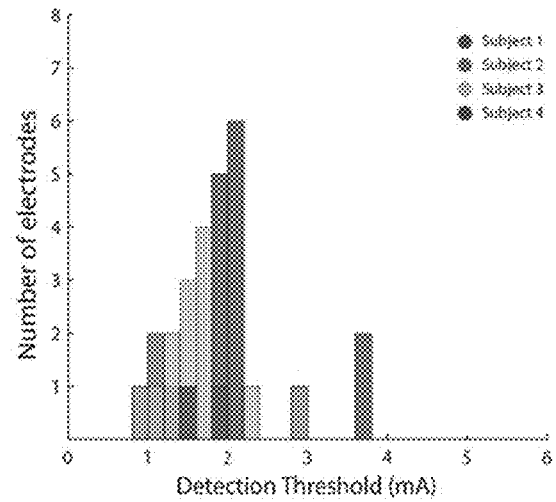

Psychophysical assessment of evoked percepts. For a subset of electrode combinations that resulted in focal percepts in the missing limb, the detection threshold was quantified using a two-alternative forced-choice paradigm. Subjects 2 and 3 were asked to focus only on the distal percept whenever stimulation co-evoked a sensation in the residual limb. In this task, the subject reported which of two intervals contained the stimulus train. With a randomized presentation of various stimulation amplitudes, the detection threshold was measured as the minimum amplitude at which the subject could correctly report the interval containing the stimulation train with 75% accuracy (FIG. 5A). Mean detection thresholds (FIG. 5B) were 3.44±0.54 mA (n=3 electrodes), 1.25±0.36 mA (n=5 electrodes), 1.66±0.50 mA (n=14 electrodes) and 1.98±0.16 mA (n=12 electrodes) in Subjects 1-4, respectively.

Figure 5C:
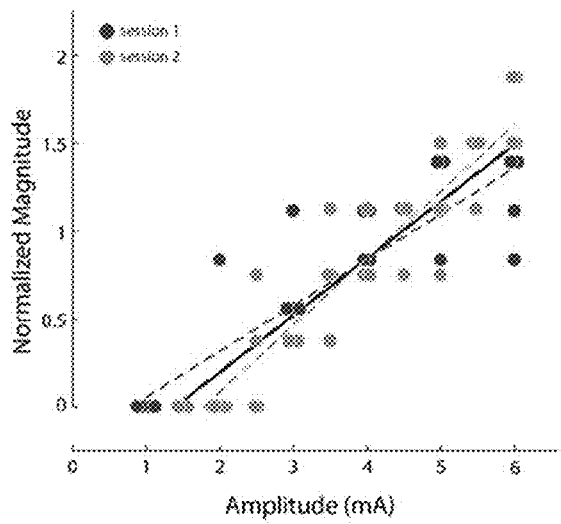
Figure 5D:
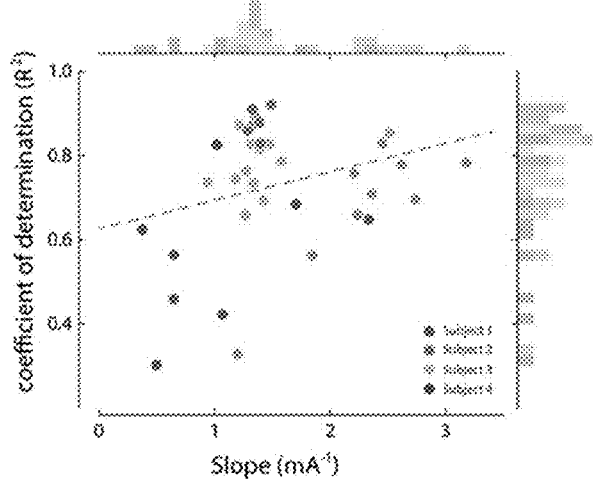
Figure 5E:
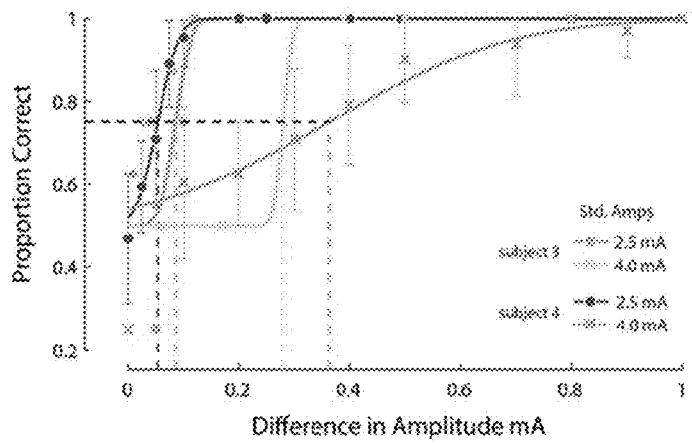

The sensitivity to changes in intensity of the evoked percepts was characterized by determining the just-noticeable differences (JND) in stimulation amplitude. In Subject 4, JNDs were determined at two different standard amplitudes for 5 individual electrodes. While the subject could perceive a mean change of 53 µA at 75% accuracy when the standard amplitude was 2.5 mA, a higher standard amplitude of 4 mA increased the mean JND to 360 µA (FIG. 5E, purple trace). In subject 3, the one electrode that was tested using both standard amplitudes, showed a similar trend (JND2.5=86 µA and JND4.0=280 µA; FIG. 5E, yellow trace). This suggests that SCS is strongly affected by Weber's law, which should be accounted for when using this approach in a somatosensory neuroprosthesis.

It was also observed that increasing the stimulation amplitude resulted in an increase in the sensation intensity. As stimulation amplitude was increased, the perceived intensity increased linearly for all subjects; an effect that was consistent across repetitions of the task on multiple days (FIG. 5C). A linear fit was determined to be better than or at least as good as a sigmoid or logarithmic fit based on the adjusted R2 values. All electrodes tested in the subjects, FIG. 5D) had a significant linear relationship between stimulus amplitude and perceived intensity, (p<0.001, F-test) with a median coefficient of determination (R2) of 0.56 (range: 0.24 to 0.80, 8 electrodes), 0.67 (range: 0.41 to 0.83, 9 electrodes) and 0.83 (range: 0.67 to 0.88, 12 electrodes) and 0.89 (range: 0.83 to 0.92, 8 electrodes) for Subjects 1-4, respectively. This linear relationship between amplitude and intensity was maintained across electrodes, even though different electrodes were tested with different pulse widths and frequencies. Table 3 shows a complete list of stimulation parameters used for free magnitude estimation experiments. There was a weak correlation ($r=0.28$) between the slope of the regression line and $R^2$ suggesting that electrodes with a steeper slope had a stronger linear relationship with intensity. This may be a result of a ceiling effect for electrodes with low slopes and wide dynamic ranges, because our stimulator could only deliver currents up to 6 mA.

TABLE 3

Summary of psychophysics testing for each subject. For detection and discrimination trials the threshold (TH) and JND per stimulation channel is listed along with the corresponding frequency and pulse width that was used.

| Subject | Electrode | Receptive Field | Minimum modal amplitude (mA) | Detection TH (mA) | Detection F (Hz) | Detection PW (ms) | JND (low) | JND (high) | Discrimination F (Hz) | Discrimination PW (ms) | Magnitude estimation Slope | Magnitude estimation $R^2$ |
|---|---|---|---|---|---|---|---|---|---|---|---|---|
| 1 | 1 | D1-D2 | 5.48 | 2.05 | 100 | 200 | | 618 | 100 | 1000 | 0.37 | 0.62 |
| | 2 | Palm (ulnar) | 5.0 | 1.86 | 100 | 800 | | | | | 1.07 | 0.42 |
| | 3 | Palm (ulnar) | 4.0 | 2.13 | 100 | 200 | | | | | 1.7 | 0.68 |
| 2 | 1 | Hand | 4.0 | 1.14 | 20 | 200 | | | | | 3.18 | 0.78 |
| | 2 | Thumb | 3.0 | 1.21 | 20 | 200 | 245 | | 50 | 200 | 2.36 | 0.71 |
| | 3 | Hand | 4.0 | | 20 | | | | | | 2.21 | 0.76 |
| | 4 | Palm, D1 | 3.0 | 1.11 | 20 | 200 | | | | | 2.74 | 0.7 |
| | 5 | Thumb | 3.0 | 0.92 | 50 | 200 | | | | | 1.2 | 0.33 |
| 3 | 1 | Hand | 6.0 | 1.98 | 50 | 200 | | | | | 0.94 | 0.74 |
| | 2 | Hand | 5.0 | 2.85 | 50 | 200 | | | | | 1.33 | 0.73 |
| | 3 | Hand | 5.0 | 1.77 | 50 | 200 | 151 | | 50 | 200 | 1.27 | 0.76 |
| | 4 | Palm, D1-D4 | 3.0 | 0.97 | 50 | 200 | | | | | | |
| | 5 | Palm, D3-D4 | 4.0 | 1.28 | 50 | 200 | | | | | 1.22 | 0.87 |
| | 6 | Palm, D1-D4 | 5.0 | 1.53 | 50 | 200 | | | | | 1.18 | 0.74 |
| | 7 | Palm, D1-D4 | 4.0 | | 50 | 200 | | | | | 1.58 | 0.79 |
| | 8 | Palm, D3-D4 | 5.0 | 1.65 | 50 | 200 | | | | | 1.39 | 0.81 |
| | 9 | Palm, D2-D4 | 3.0 | | 50 | 200 | | | | | 1.43 | 0.69 |
| 4 | 1 | Hand | 3.0 | 1.52 | 50 | 200 | | | | | | |
| | 2 | D2, D4 | 4.0 | 2.13 | 50 | 200 | | | | | | |
| | 3 | D2 | 2.0 | | 50 | 200 | | | | | | |
| | 4 | D1, D2 | 3.0 | 2.05 | 50 | 200 | 62 | 222 | 50 | 200 | 1.37 | 0.88 |
| | 5 | Thumb, D1, D2 | 3.0 | 2.13 | 50 | 200 | | 527 | 50 | 200 | 1.39 | 0.83 |
| | 6 | Thumb, D1, D2 | 3.0 | | 50 | 200 | | | | | 1.33 | 0.87 |
| | 7 | Thumb, D1 | 3.0 | 1.97 | 50 | 200 | | | | | | |
| | 8 | Thumb, D1 | 3.0 | 1.98 | 50 | 200 | 27 | 647 | 50 | 200 | 1.49 | 0.92 |
| | 9 | Palm, Thumb, D1-D3 | 3.0 | 2.05 | 50 | 200 | 59 | 516 | 50 | 200 | 1.32 | 0.91 |
| | 10 | D2, D3 | 3.0 | 1.99 | 50 | 200 | 44 | 488 | 50 | 200 | 1.29 | 0.86 |
| | 11 | Thumb, D1, D2 | 3.0 | 2.01 | 50 | 200 | 54 | 300 | 100 | 200 | 1.32 | 0.91 |
| | 12 | Hand | 3.0 | | 50 | 200 | | | | | | |
| | 13 | Hand | 3.0 | | 50 | 200 | | | | | | |
| | 14 | Hand | 2.0 | 1.95 | 50 | 200 | | | | | | |
| | 15 | Hand | 3.0 | 2.1 | 50 | 200 | | | | | | |
| | 16 | Thumb, D1 | 3.0 | 1.86 | 50 | 200 | 96 | 360 | 50 | 200 | 1.36 | 0.89 |

In order to examine the effects of the stimulation parameters on the intensity of the evoked sensation for each categorical modality descriptor, a series of generalized linear models (GLM) was created combining data from all 4 subjects using SAS/STAT® software. For sensations reported as 'mechanical', the pulse width and amplitude of stimulation had significant effect ($p<0.001$) on the reported sensation. Specifically, for every unit increase in amplitude there was a 0.376 unit increase in 'mechanical' intensity whereas pulse width had a weak effect (<0.01 unit increase) on intensity. For sensations reported as 'tingle' there was a significant main effect of amplitude (p values <0.001). For every unit increase in amplitude, there was a 0.362 unit increase in tingle intensity, although there was significant inter-subject variability. Similarly, for 'movement' sensations there were significant main effects of pulse width, amplitude, and frequency (p values <0.001). For every unit increase in amplitude and frequency there was a 0.568, and 0.016 unit increase in the intensity of the sensation respectively, while pulse width had a weak effect (<0.01 unit increase) on intensity.

Effect of stimulation parameters on perceptual quality of evoked percepts. In general, varying the stimulation frequency influenced the modality of the evoked sensation in Subject 3, but not in the other subjects. The sensory percepts that were described as "touch" or "pressure" occurred in up to 90% of trials at low stimulation frequencies (below 20 Hz) while stimulation frequencies above 50 Hz evoked percepts that were always characterized as paresthesia. Subject 1 never reported these naturalistic sensations which could be because we never stimulated at frequencies below 20 Hz while Subject 2 and 4 respectively reported them 40% and 30% of the time irrespective of the stimulus frequency.

Furthermore, we utilized a Naive Bayes classifier using IBM SPSS Modeler® to predict the categorical descriptors for 'movement', 'mechanical', and 'tingle' from stimulation parameters, subject, and time since implant. When the evoked percept had a 'movement' component, our model correctly predicted the sensations 82.87% of the time; accurately predicting the vibration sensation 98.8% of the time. When the evoked percept had a 'mechanical' component, our model correctly predicted the sensations 63.28% of the time; accurately predicting the pressure sensation 90.88% of the time, sharp 21.77% of the time, and touch 12% of the time. When the evoked percept contained a 'tingle' component, our model correctly predicted the sensations 76.34% of the time; accurately predicting the electrical sensation 89.31% of the time, tickle 57.29% of the time, and pins and needles 33.33% of the time.

The most important predictor of the 'movement' and 'tingle' components was subject. This observation agrees with our outcomes from the GLM. A significant inter-subject variability in the effect of stimulation parameters on movement and tingle would explain the higher weightage to subject in the Naïve Bayes classifier. This result also suggests that some subjects were more likely to report these sensations than others. The most important predictor of the mechanical sensation was amplitude which would also indicate that the effect of stimulation parameters on mechanical sensation was consistent across subjects.

Figure 6B:
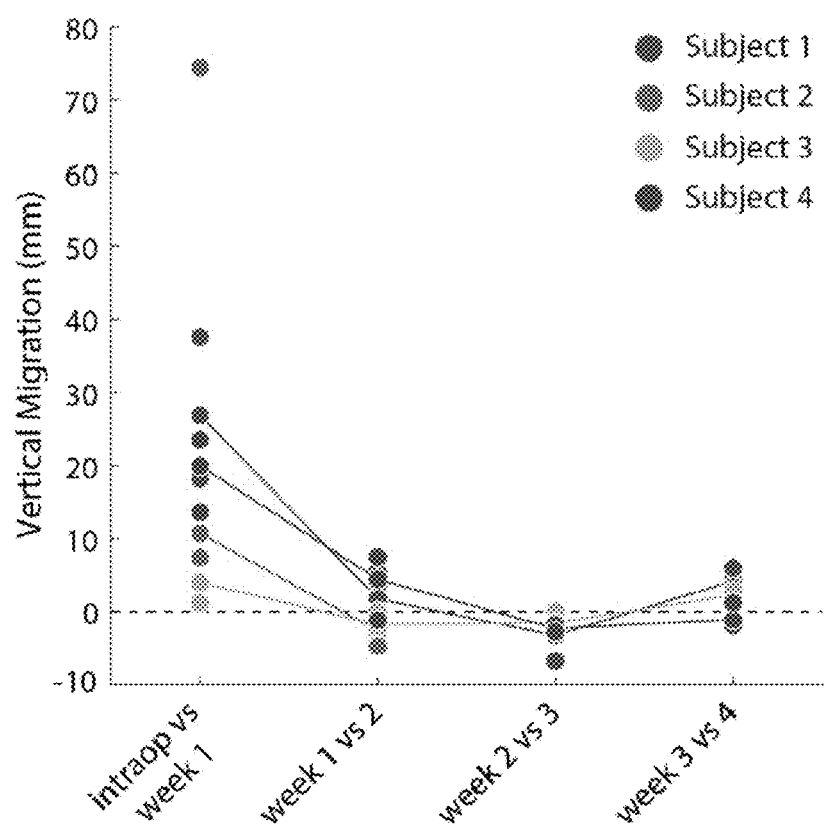

Stability of SCS electrodes and evoked sensory percepts. Lead migration is a common clinical complication for SCS, with an incidence rate as high as 15-20%. Lead migration would result in instability in the electrode tissue interface and may change the location and modality of evoked sensations. Weekly X-rays were performed to monitor the position of the leads and quantify migration over the duration of the implant. Superimposing the intraoperative fluoroscopy image and the final X-ray (FIG. 6A) revealed that lead migration was largely restricted to the rostro-caudal axis. In all subjects, the largest caudal migration was observed when comparing the intraoperative fluoroscopy image with the X-ray from the first week (FIG. 6B). One of the leads in Subject 2 almost completely migrated out of the epidural space in this post-operative period (FIG. 6B), rendering it unusable for stimulation experiments. In contrast to the migration that occurred during the first week, X-rays from the first and last week of testing showed minimal lead migration. This was further corroborated by the week-to-week migration of the rostral tip of each lead (FIG. 6B). In the weeks following the initial migration, the median migration in the rostro-caudal direction across the three leads in any subject never exceeded 5 mm. Moreover, with each successive subject, the caudal migration of the leads in the time period between the intraoperative fluoroscopy and the first X-ray decreased from a median of 27 mm (range: 18-38 mm) in Subject 1 to a median of 11 mm (range: 7-74 mm) in Subject 2 and 4 mm (range: 1-4 mm) in Subject 3. We observed a higher median migration of 20 mm (range: 13-23 mm) in subject 4. However, the initial placement of the leads rostral to the target cervical levels prevented loss of coverage of those spinal levels following the caudal migration of the leads. This suggests that iterative improvements in our lead placement technique may have helped alleviate this initial lead migration or at least mitigate the consequent loss of coverage of target cervical levels.

Figure 7:
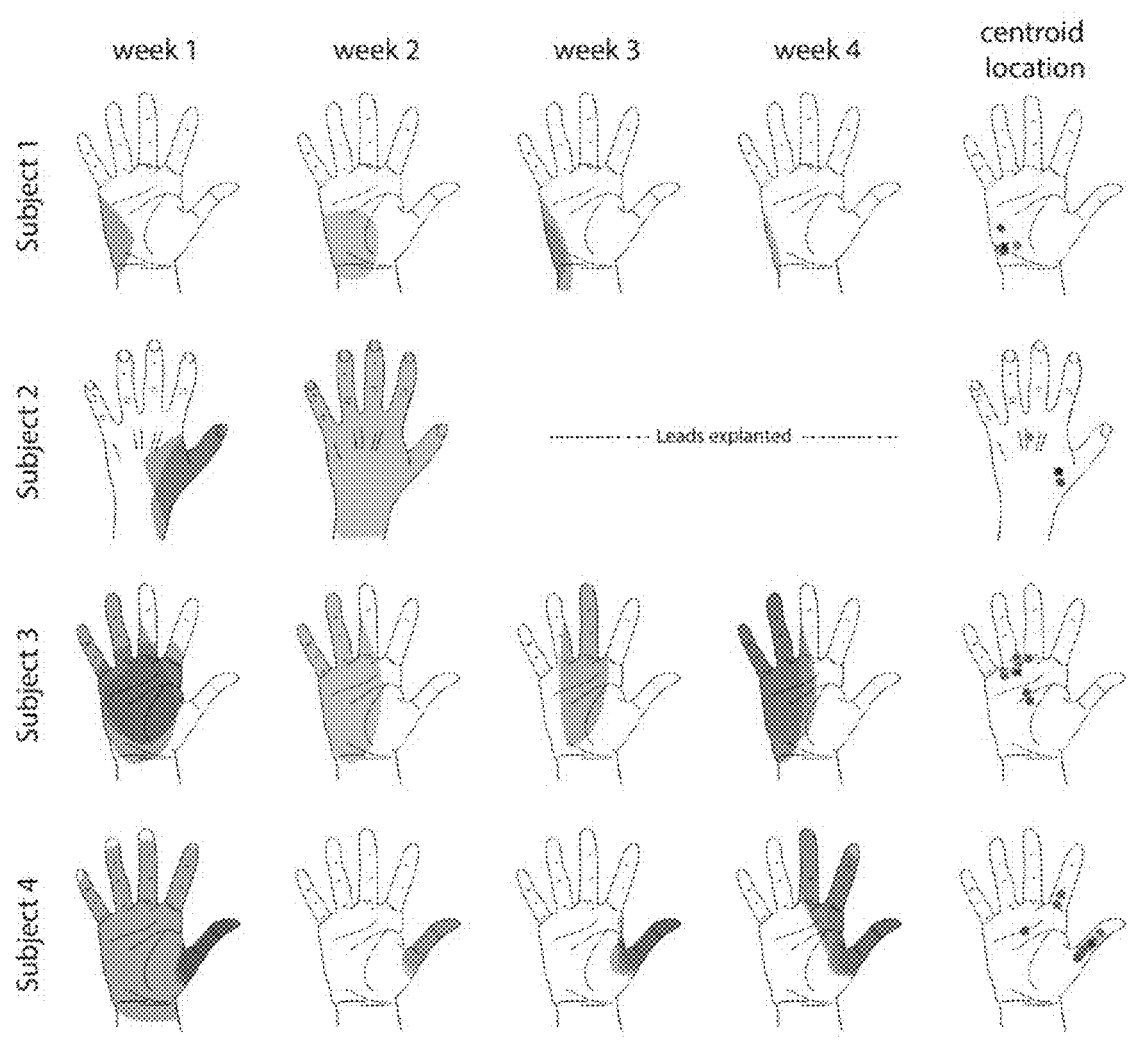
FIG. 7: Stability of the sensory percepts. Example sensory percepts form the hand for a single electrode in Subjects 1-4. For Subject 2, the percepts are shown for weeks 1 and 2 only, as the leads were explanted after that. The percepts shown were evoked by the minimum stimulus amplitude that was tested at least once per week for the maximal number of weeks (minimum modal amplitude). The first four columns show the percepts evoked for each week of testing. Multiple examples of the percepts evoked during the week are superimposed on each other. The fifth column shows the location of the centroid for each percept (filled circle) and the median centroid (X) across all weeks for that electrode. The distance of individual percept centroids from the median centroid was used as one metric of stability. The centroid distances and changes in percept area over time for all electrodes are shown in FIG. 11.
Figure 11A:
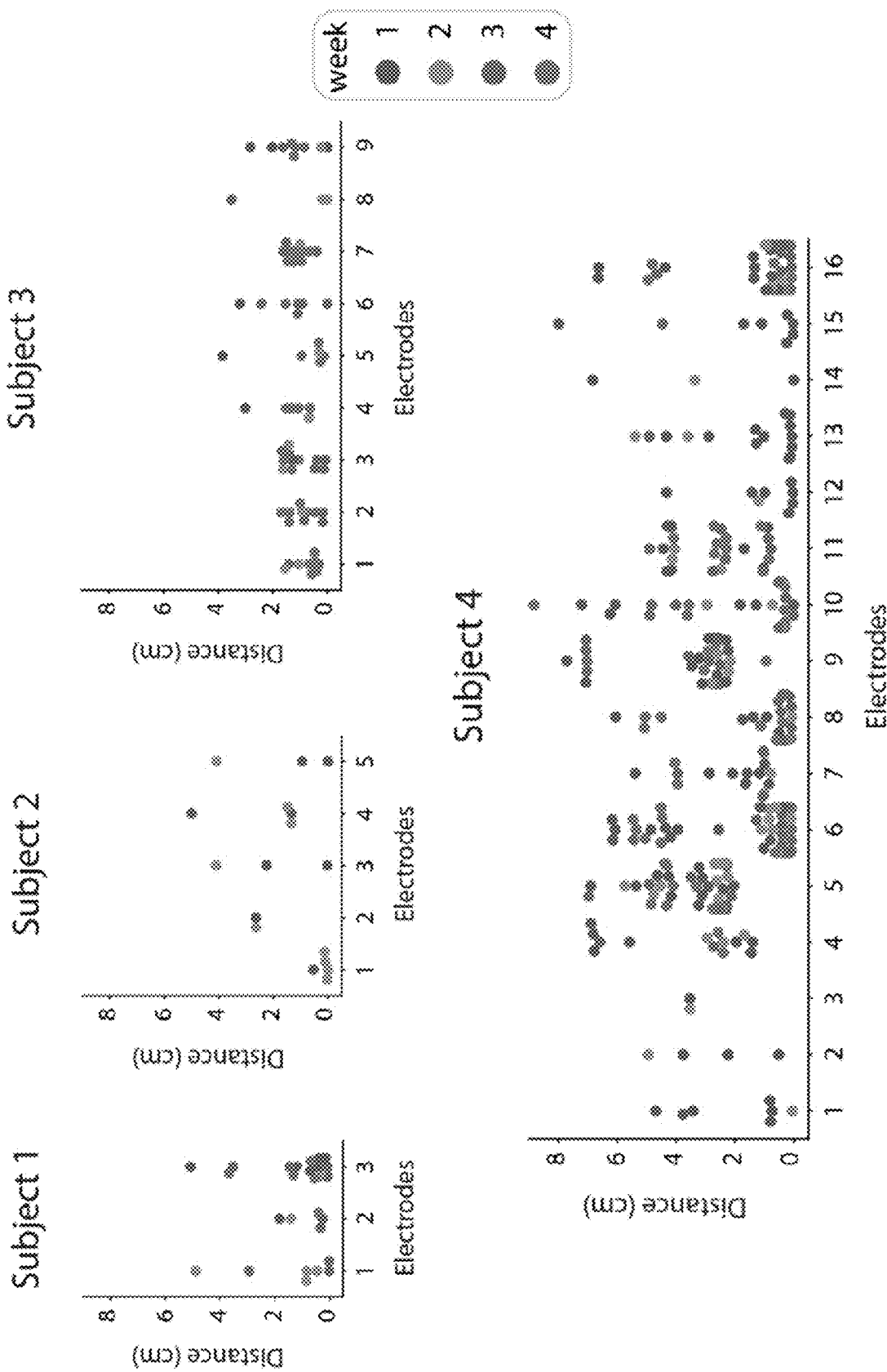
FIGS. 11A and 11B. Stability of the (FIG. 11A) centroid and (FIG. 11B) area of evoked percepts for each electrode for subjects 1-4. The distance between the centroid of each occurrence of a given percept and the location of the median of all centroids of the percept is shown in filled circles (FIG. 11A). For FIG. 11B, each point represents the change in area of the evoked percept when compared to the median area for a given electrode, expressed as a fraction of the total area of the hand. Each point is colored based on the week wherein the corresponding percept was reported.
Figure 11B:
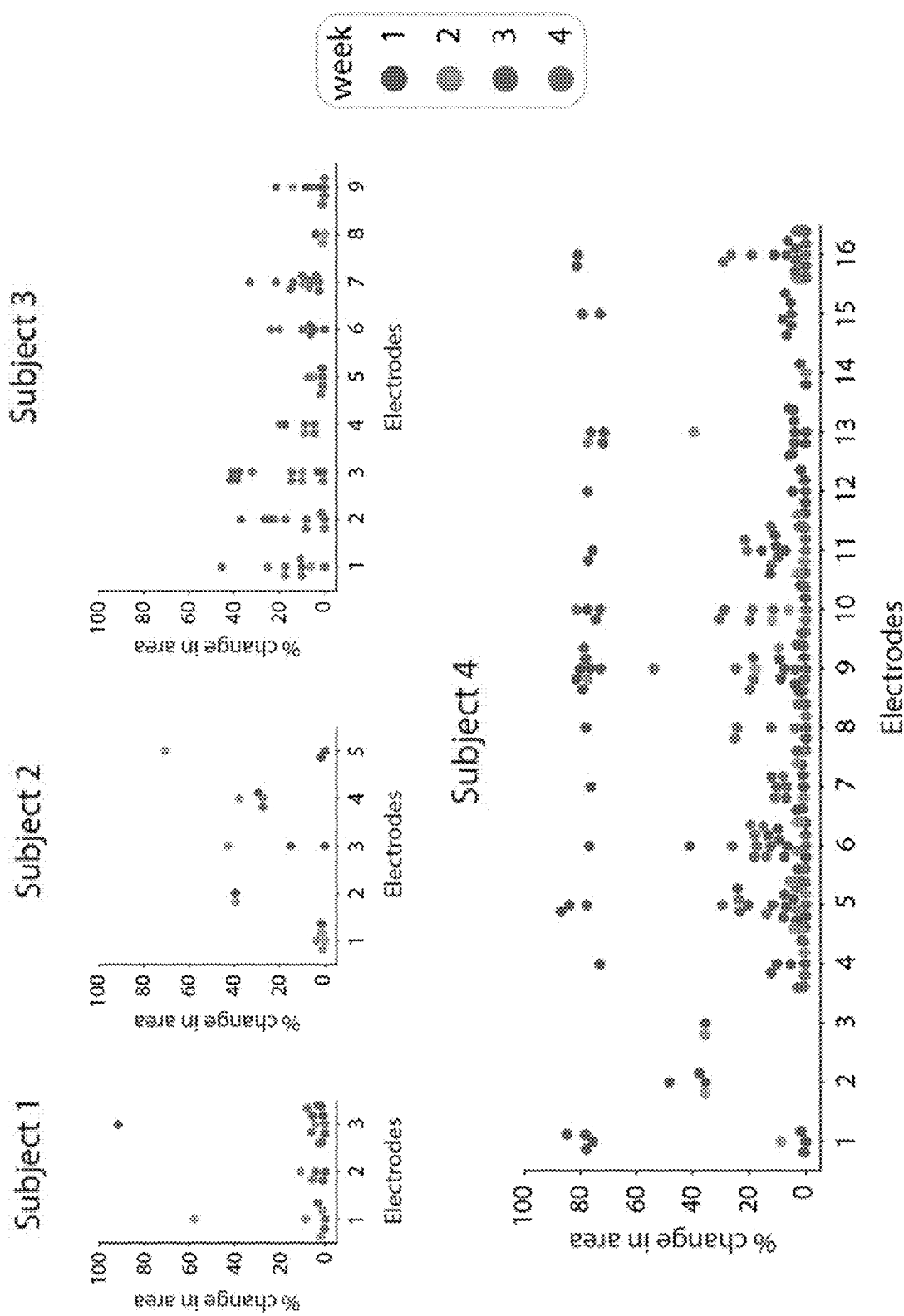

The stability of each evoked percept was assessed throughout the duration of the study in terms of its size (area) and location (centroid) (FIG. 7). The centroid and area were calculated for all percepts evoked by the smallest stimulus amplitude that was tested at least once each week for the highest number of weeks during the implant. The migration of these centroids was quantified with respect to the median location of all centroids for each electrode (FIG. 11A). In the missing hand, the location of evoked percepts exhibited a median migration ranging from 1.2 to 35.3 mm. Similarly, the change in area for each evoked percept was calculated with respect to the median area and normalized to the total are of the hand (FIG. 11B). The median change in area of percepts evoked in the missing hand ranged from 0 to 40% of the total area of the hand. Individual percepts that had a centroid migration within the 75th percentile and percentage change in area less than 20% were considered stable. Of the total 494 relevant percepts, 322 percepts had a stable area and centroid location while 126 percepts satisfied one of the two conditions for stability. We constructed two separate auto-regressive time series model to examine the changes in distributions of area and centroid distance over time, adjusting for autocorrelations in the data. Results demonstrated a significant decrease in area over time across all weeks, $b=-0.2013$, $p<0.001$. For centroid distance, there was a decrease in the distribution during weeks 2 ($b=-23.224$, $p=0.02$) and 3 ($b=-40.585$, $p<0.001$).

Since the open-ended magnitude estimation task demonstrated a consistent linear relationship between intensity of percept and stimulation amplitude, the concomitant changes in percept area that may occur as stimulation amplitude is increased were quantified. In the context of clinical translation, being able to modulate the intensity of the percept independent of the area is critical to deliver graded feedback that remains focal. To examine the effects of stimulation amplitude on the area and intensity of the evoked percept, separate GLM models for each outcome were constructed, and analyzed the effect of the stimulation parameters using Type III sum of squares. Results indicated that stimulation amplitude, had a significant effect on both area and intensity of evoked percepts while there was significant inter-subject variability. For every unit increase in amplitude, there was a 0.16 unit increase in area ($p<0.001$) and a 1.1 unit increase in intensity ($p<0.001$) across all subjects. This would indicate that while percept area is not entirely independent of stimulation amplitude, the unit change in intensity is almost an order of magnitude larger than the unit change in area with respect to stimulation amplitude.

DISCUSSION

This example demonstrates that epidural SCS has the potential to be an effective and stable approach for restoring sensation in people with upper-limb amputations. Sensory percepts were evoked that were focal and localized to the distal missing limb. The repertoire of sensory percepts elicited varies across subjects and thus, this approach would require user-dependent characterization. The intensity of the evoked sensations could be modulated by varying stimulation amplitude with only a minor increase in the perceived area of the evoked sensations.

SCS-evoked sensory percepts were perceived to emanate from the missing limb in all subjects. Multipolar stimulation allowed the evocation of sensations that were localized to distal regions of the missing hand and wrist, as compared to monopolar stimulation, which primarily evoked sensations in the forearm and upper arm in all except Subject 4. In all subjects, the leads were steered toward the lateral spinal cord and spinal roots, ipsilateral to the amputation. At this location, the dorsal rootlets fan out under the dura before entering the spinal cord at the dorsal root entry zone. Previous work has shown that in the cervical spinal cord, the rootlets are each approximately 0.4-1.3 mm in diameter and densely packed with few spaces between them. This arrangement, superficially resembling the flattened peripheral nerve cross-section achieved by the flat interface nerve electrode, may lend itself to a higher degree of selective activation than could be achieved with stimulation of more traditional SCS targets such as the dorsal columns or the dorsal root ganglia. The relationship between the locations of the electrodes and that of the evoked percepts showed marked inter-subject variability and deviation from established dermatome maps. For example, all electrodes in Subject 1 were in the T1 region, but the subject reported sensations in the missing hand, a region covered by the C6-C8 dermatomes.

Evoking naturalistic sensations has been a primary aim for somatosensory neuroprosthetic systems, and a number of stimulation paradigms, such as varying charge density (Charkhkar et al., J Neural Engineering, 15(5):56002, 2018), modulating pulse width (Tan et al. Int IEEE/EMBS Conf Neural Engineering, NER, 12(2):859-862, 2015), or more complex biomimetic stimulus trains (Okorokova et al., J Neural Engineering, 9, 2018; Valle et al., Neuron, 100:1-9, 2018) have been proposed to evoke more naturalistic sensations, though none of these approaches have established a stimulation paradigm that reliably elicits naturalistic sensations across subjects. The ability to evoke naturalistic percepts via the clinically translatable approach provided in this example in individuals with high-level amputations shows the surprising effectiveness of this example towards restoring sensation.

The location of the implanted SCS electrodes and the corresponding evoked percepts showed only minor migration across the duration of implantation. In clinical practice, SCS lead migration is a common complication, occurring in as many as 15-20% of cases, and is typically classified by a complete loss of paresthetic coverage of the region of interest. Repeated monitoring of both the physical location of the SCS leads and the evoked paresthesias demonstrated that there was some migration immediately after implantation, but minimal movement thereafter. As a preemptive measure against loss of coverage due to the initial migration, longer 16-contact leads were uses in the second, third, and fourth subjects. By placing the leads such that the most rostral contacts were above the target spinal levels, continued coverage was ensured even in the case of caudal migration. While it was encouraging to observe a reduction in the initial migration with each successive implant, it is worth noting that these leads were not anchored to any bony structures or nearby tissue. Future permanently implanted systems for restoring sensation using SCS can utilize these anchoring techniques and thereby reduce or eliminate lead migration (Mekhail et al., Pain Practice, 11(2):148-153, 3 2011). The stability in the electrodes is reflected in the stability of the evoked percepts. In the hand region, a migration of evoked percepts of 1-35 mm was observed, which is similar to the shift reported in peripheral stimulation approaches (Tan et al. Int IEEE/EMBS Conf Neural Engineering, NER, 12(2):859-862, 2015). Moreover, given that the spatial acuity in the palm region is approximately 8-10 mm, the scale of migration observed is within the range that would not likely be detectable by the user.

Since this approach described in this example targets proximal neural pathways, SCS mediated sensory restoration lends itself to use for a wide range of populations, such as individuals with proximal amputations and those with peripheral neuropathies in which stimulation of peripheral nerves may be difficult or impossible. Provided that the injury does not affect the dorsal roots and spinal cord, the results suggest that these techniques can be effective in restoring sensation, regardless of the level of limb loss. Moreover, the widespread clinical use of SCS and the well-understood risk profile provide a clear pathway towards clinical adoption of these techniques for a somatosensory neuroprostheses.

Example 2

Spinal Rootlet and Lateral Spinal Cord Stimulation to Improve Prosthesis Control and to Reduce Phantom Limb Pain in Lower-Limb Amputees This example illustrates the effectiveness of stimulating the spinal rootlets and the spinal cord in lower-limb amputees to reduce phantom limb pain.

Two subjects with lower limb amputation were selected for assessment.

Subject 1 had a trans-tibial amputation approximately one year prior to the study caused due to dysvascular disease. Subject 2 had an elective amputation caused by a non-healing wound seven years prior to the study.

A neurostimulator with three multi-channel electrodes targeting the lateral lumbosacral spinal cord and dorsal rootlets was implanted into each subject. The electrodes of the stimulator were tunneled percutaneously and into the dorsal epidural space adjacent to the lateral spinal cord and the dorsal rootlets as described in Example 1. Localization was targeted to spinal regions corresponding to the amputated limb and accomplished using the stylet included with the spinal rootlets/cord stimulator electrodes to steer the electrodes laterally into position under fluoroscopic guidance. Once in place, the leads were secured in place with tape or suture. The leads remained in the epidural space for less than 30 days before removal.

Figure 12:
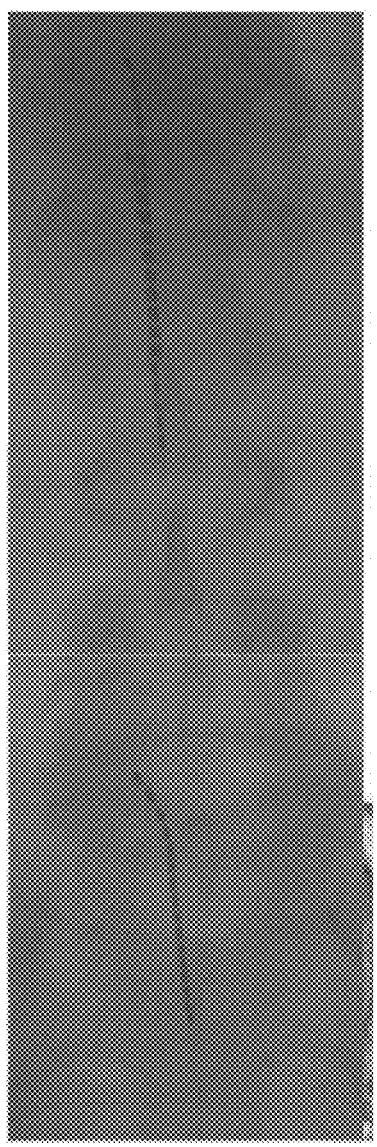
FIG. 12 shows an intraoperative fluoroscopy image showing the placement of neurostimulator electrodes in the lumbar region of Subject 4.

As an illustration, FIG. 12 shows the placement of the electrodes in Subject 1 by intraoperative fluoroscopy and follow-up X-ray. As shown, the leads are primarily targeting the lateral spinal cord and dorsal rootlets.

Following implantation, the electrodes were connected to an external stimulator and a series of psychophysical evaluations were conducted to characterize the sensory percepts evoked by epidural stimulation. Stimulation amplitude, pulse duration, and frequency ranged 0-6 mA, 50-1000 µs, and 1-1000 Hz, respectively.

To assess sensation due to stimulation in each subject, stimulation was applied and the subjects were asked to describe the location and type of induced sensation. The location of stimulation-induced sensation for Subject 1 is depicted in FIG. 13.

After each stimulus presentation, subjects reported instantaneous phantom limb pain. Subjects completed McGill Pain Questionnaire weekly to report overall pain level. As shown in in FIG. 14, a decrease in McGill pain score resulted during the trial.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

It is claimed:

1. A method for reducing phantom limb pain or diabetic neuropathy pain in a subject, comprising:
   providing a therapeutically effective amount of stimulation to dorsal rootlets, or lateral spinal cord adjacent to the dorsal rootlets, of one or more sensory neurons innervating a limb of the subject with the phantom limb pain or the diabetic neuropathy pain; and wherein:
   the stimulation is provided with one or more electrodes of a neurostimulator that are implanted at the dorsal rootlets or the lateral spinal cord adjacent to the dorsal rootlets of the one or more sensory neurons innervating the limb of the subject;
   the one or more electrodes are activated to provide the stimulation in response to activation of a sensor detecting movement and/or position of the limb or movement and/or position of a physical or virtual prosthesis of the limb; and
   the stimulation reduces the phantom limb pain or diabetic neuropathy pain in the subject.

2. The method of claim 1, further comprising calibrating the stimulation to induce sensations of pressure, touch, movement, proprioception, and/or kinesthesia at the location of the phantom limb pain or diabetic neuropathy pain in the subject.

3. The method of claim 1, wherein stimulating the dorsal rootlets or the lateral spinal cord does not cause paresthesia in the limb with the phantom limb pain or diabetic neuropathy pain.

4. The method of claim 1, wherein the neurostimulator is an external or implanted pulse generator.

5. The method of claim 1, further comprising implanting the neurostimulator in the subject.

6. The method of claim 1, wherein the sensor is any one of a gyroscope, an electrogoniometer, a textile piezoresistive sensor, or a pressure sensor located in or on the limb or the prosthesis of the subject.

7. The method of claim 1, wherein the sensor detects pressure at the fingertips of a prosthetic hand or in the sole of a prosthetic foot.

8. The method of claim 1, wherein the sensor detects a position of the limb or the physical or virtual prosthesis of the limb.

9. The method of claim 1, wherein the virtual prosthesis of the limb is a computer-generated image of the limb the movement of which is observed or controlled by the subject.

10. The method of claim 1, further comprising selecting the subject with the phantom limb pain or diabetic neuropathy pain for treatment.

11. The method of claim 1, wherein providing the therapeutically effective amount of stimulation comprises applying electrical stimulation at a frequency of from 1-300 Hz, an amplitude of from 0.1-10 mA, and a pulse duration of from 50-500 µsec, to the dorsal rootlets or the lateral spinal cord adjacent to the dorsal rootlets innervating the limb of the subject.

12. The method of claim 1, wherein the neurostimulator is implanted at the dorsal rootlets of the sensory neurons innervating the limb of the subject.

13. The method of claim 1, wherein the neurostimulator is implanted at the lateral spinal cord adjacent to the dorsal rootlets of the sensory neurons innervating the limb of the subject.

14. The method of claim 1, wherein treating the phantom limb pain or diabetic neuropathy pain comprises at least a 50% decrease in pain as measured using the McGill pain score.

15. A method for increasing control of a prosthetic limb of a subject, comprising:
    providing a therapeutically effective amount of stimulation to dorsal rootlets, or lateral spinal cord adjacent to the dorsal rootlets, of sensory neurons innervating an amputated limb of the subject, wherein the subject uses a prosthesis of the amputated limb; and wherein:
    the stimulation is provided with one or more electrodes of a neurostimulator that are implanted at the dorsal rootlets or the lateral spinal cord adjacent to the dorsal rootlets of the sensory neurons innervating the amputated limb;
    the one or more electrodes are activated to provide the stimulation in response to activation of a sensor detecting movement and/or position of a stump of the limb or the prosthesis or in response to movement and/or position of a virtual prosthesis of the limb; and
    the stimulation improves control of the prosthesis of the limb by the subject.

16. The method of claim 15, further comprising calibrating the stimulation to induce sensations of pressure or touch in the amputated limb.

17. The method of claim 15, wherein stimulating the dorsal rootlets or the lateral spinal cord does not induce paresthesia in the amputated limb.

18. The method of claim 15, wherein the neurostimulator is an external or implanted pulse generator.

19. The method of claim 15, further comprising implanting the neurostimulator in the subject.

20. The method of claim 15, wherein the sensor is any one of a gyroscope, an electrogoniometer, a textile piezoresistive sensor, or a pressure sensor located in or on the limb or the prosthesis of the subject.

21. The method of claim 15, wherein the sensor detects pressure at the fingertips of a prosthetic hand or in the sole of a prosthetic foot.

22. The method of claim 15, wherein the sensor detects a position of the limb, the stump of the limb, the prosthesis, or the virtual prosthesis.

23. The method of claim 15, wherein the virtual prosthesis of the limb is a computer-generated image of the limb and the movement of the computer-generated image of the limb is observed or controlled by the subject.

24. The method of claim 15, further comprising selecting the subject with the amputated limb with the prosthesis for treatment.

25. The method of claim 15, wherein providing the therapeutically effective amount of stimulation comprises applying electrical stimulation at a frequency of from 1-300 Hz, an amplitude of from 0.1-10 mA, and a pulse duration of from 50-500 μsec, to the dorsal rootlets or the lateral spinal cord adjacent to the dorsal rootlets innervating the amputated limb of the subject.

26. The method of claim 15, wherein the neurostimulator is implanted at the dorsal rootlets of the sensory neurons innervating the amputated limb of the subject.

27. The method of claim 15, wherein the neurostimulator is implanted at the lateral spinal cord adjacent to the dorsal rootlets of the sensory neurons innervating the amputated limb of the subject.

28. The method of claim 15, wherein increasing control of the prosthetic limb of the subject increases postural balance in the subject by at least 50% as measured using a sensory organization test.

* * * * *